(12) United States Patent
Lee et al.

(10) Patent No.: US 11,668,709 B2
(45) Date of Patent: Jun. 6, 2023

(54) SYSTEM FOR MONITORING POST-TRANSLATIONAL MODIFICATION OF PROTEIN USING BIO-SENSOR WITH GAP AND MANUFACTURING METHOD FOR BIO-SENSOR

(71) Applicant: KOREA INSTITUTE OF SCIENCE AND TECHNOLOGY, Seoul (KR)

(72) Inventors: Soo Hyun Lee, Seoul (KR); Ji Yoon Kang, Seoul (KR); Hyewhon Rhim, Seoul (KR); Yi Jae Lee, Seoul (KR); Hyewon Seo, Seoul (KR); Yun Kyung Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 16/579,852

(22) Filed: Sep. 24, 2019

(65) Prior Publication Data
US 2020/0110099 A1    Apr. 9, 2020

(30) Foreign Application Priority Data

Oct. 4, 2018 (KR) .................. 10-2018-0118415
Jul. 12, 2019 (KR) .................. 10-2019-0084599

(51) Int. Cl.
*G01N 33/543* (2006.01)
*G01N 33/68* (2006.01)
*G16B 40/10* (2019.01)

(52) U.S. Cl.
CPC . *G01N 33/54373* (2013.01); *G01N 33/54326* (2013.01); *G01N 33/6845* (2013.01);
(Continued)

(58) Field of Classification Search
None
See application file for complete search history.

(56) References Cited

U.S. PATENT DOCUMENTS

| 6,144,871 A * | 11/2000 | Saito | C12Q 1/006 600/345 |
| 2006/0073489 A1* | 4/2006 | Li | B01D 57/02 435/6.11 |
| 2008/0149479 A1* | 6/2008 | Olofsson | B82Y 30/00 204/403.14 |

(Continued)

FOREIGN PATENT DOCUMENTS

| JP | 2013-521942 A | 6/2013 |
| KR | 1020130091288 A | 8/2013 |

(Continued)

OTHER PUBLICATIONS

Waltraud Mair et al., "FLEXITau: Quantifying Post-translational Modifications of Tau Protein in Vitro and in Human Disease," Anal. Chem., Apr. 5, 2016, 3704-3714.
(Continued)

*Primary Examiner* — Melanie Brown
(74) *Attorney, Agent, or Firm* — Cantor Colburn LLP

(57) ABSTRACT

The present disclosure relates to a system for monitoring post-translational modification of protein using a biosensor with a gap, which performs with high reliability a diagnosis of a disease associated with a target protein for which impedance is measured, by measuring an impedance of a sample introduced into a sensor and calculating a change rate of the measured impedance, and to a method of manufacturing the biosensor used for the system.

7 Claims, 41 Drawing Sheets

(52) U.S. Cl.
CPC ......... *G01N 33/6896* (2013.01); *G16B 40/10* (2019.02); *G01N 2440/00* (2013.01); *G01N 2440/14* (2013.01); *G01N 2440/38* (2013.01); *G01N 2800/2821* (2013.01)

(56) References Cited

U.S. PATENT DOCUMENTS

| | | | |
|---|---|---|---|
| 2010/0193358 A1* | 8/2010 | Hamada | G01N 15/0656 204/547 |
| 2010/0331194 A1* | 12/2010 | Turner | G01N 27/447 506/2 |
| 2011/0033910 A1* | 2/2011 | Yamanaka | G01N 33/5438 435/308.1 |
| 2012/0326732 A1* | 12/2012 | Cho | B82Y 15/00 324/654 |
| 2017/0131233 A1* | 5/2017 | Kang | G01N 27/3275 |
| 2018/0217164 A1* | 8/2018 | Lee | G01N 33/54373 |
| 2018/0298436 A1* | 10/2018 | Lei | C12Q 1/6869 |

FOREIGN PATENT DOCUMENTS

| | | |
|---|---|---|
| KR | 10-2015-0081841 A | 7/2015 |
| KR | 1020170054171 A | 5/2017 |
| KR | 1020180089849 A | 8/2018 |

OTHER PUBLICATIONS

H.W. Seo et al., "Ultrasensitive Nanogap Sensor for Detecting Tau and Phosphorylated Tau in Blood to Diagnose Alzheimer's Disease," The 28th anniversary world congress on Biosensors, Biosensors 2018, Jun. 14, 2018, 23 pages.

Korean Office Action for KR Application No. 10-2019-0084599 dated Aug. 31, 2020, citing the above reference(s).

Korean Office Action for KR Application No. 10-2019-0084599 dated May 31, 2021, citing the above reference(s).

Korean Office Action for KR Application No. 10-2019-0084599 dated Mar. 17, 2021, citing the above reference(s).

* cited by examiner (a) 2.8um beads

Density : 1/500, 4 times (b) 4.5um beads

Density : 1/250, 4 times

FIG. 7B

| Tau | 1Hz | 10Hz | 100Hz | ΔZ [%] at 1Hz |
|---|---|---|---|---|
| PBS | 43.7M | 11.3M | 1.8M | 0 |
| Negative | 39.9M | 11.0M | 1.9M | 0 |
| 0.5 fg/mL | 37.8M | 9.7M | 1.7M | 5.3 |
| 5 fg/mL | 33.5M | 8.6M | 1.6M | 16.0 |
| 50 fg/mL | 27.7M | 4.7M | 1.2M | 30.5 |
| 500 fg/mL | 24.4M | 5.7M | 1.2M | 38.9 |
| 5 pg/mL | 20.7M | 5.0M | 1.1M | 48.2 |
| 50 pg/mL | 18.0M | 3.0M | 0.5M | 54.8 |

FIG. 10C

| | Tau (MΩ) | O-g (MΩ) | Change by O-g (%) | AT-8 (MΩ) | Change by AT-8 (%) | $Z_{ratio}$ (Taumeter) |
|---|---|---|---|---|---|---|
| PBS | 59.23 | | | | | |
| Negative | 52.75 | | | | | |
| 0μM (Control) | 39.57 | 38.27 | 2.464432 | 33.65 | 11.2344 | 4.558615 |
| 100μM | 38.95 | 35.0 | 7.477086 | 37.65 | 2.46519 | 0.329699 | change : $\dfrac{Z_{Tau} - Z_{2nd}}{Z_{neg}} \times 100$ $O = \dfrac{Z_{Tau} - Z_{2nd(o\text{-}g)}}{Z_{neg}}$ $P = \dfrac{Z_{Tau} - Z_{2nd(P)}}{Z_{neg}}$

FIG. 13C $$\text{Taumeter} = \frac{P_{change}}{0-g_{change}} \quad 0-g_{change} = \frac{z_{Tau}-z_{2nd(o-g)}}{z_{tau}}, P_{change} = \frac{z_{Tau}-z_{2nd(p)}}{z_{tau}}$$

FIG. 14C $$\text{Taumeter} = \frac{P_{change}}{O-g_{change}} \quad O-g_{change} = \frac{z_{Tau}-z_{2nd(o-g)}}{z_{tau}}, P_{change} = \frac{z_{Tau}-z_{2nd(p)}}{z_{tau}}$$

Wildtype
3month vs 12 month

| Original T-tau | | Assay T-tau | |
| --- | --- | --- | --- |
| 3month | 12month | 3month | 12month |
| 140.8 pg/ml | 193.8 pg/ml | 14.08 pg/ml | 19.38 pg/ml |

| 3month | Taumeter | 0.2568 |
| --- | --- | --- |
| 12month | Taumeter | 0.3610 |

FIG. 15C $$\text{Taumeter} = \frac{P_{change}}{O-g_{change}} \quad O-g_{change} = \frac{z_{Tau}-z_{2nd(o-g)}}{z_{tau}}, P_{change} = \frac{z_{Tau}-z_{2nd(p)}}{z_{tau}}$$

FIG. 16C $$\text{Taumeter} = \frac{P_{change}}{O-g_{change}}$$

$$O-g_{change} = \frac{z_{Tau}-z_{2nd(o-g)}}{z_{tau}}, P_{change} = \frac{z_{Tau}-z_{2nd(p)}}{z_{tau}}$$

FIG. 17C $$\text{Taumeter} = \frac{P_{change}}{O - g_{change}}$$

$$O - g_{change} = \frac{Z_{Tau} - Z_{2nd(o-g)}}{Z_{tau}}, P_{change} = \frac{Z_{Tau} - Z_{2nd(p)}}{Z_{tau}}$$

SYSTEM FOR MONITORING POST-TRANSLATIONAL MODIFICATION OF PROTEIN USING BIO-SENSOR WITH GAP AND MANUFACTURING METHOD FOR BIO-SENSOR

CROSS-REFERENCE TO RELATED APPLICATIONS

The present application claims priority to Korean Patent Application No. 10-2018-0118415 filed on Oct. 4, 2018 and No. 10-2019-0084599 filed on Jul. 12, 2019 in the Republic of Korea, the disclosure of which is incorporated herein by reference.

BACKGROUND

1. Field of the Invention

The present disclosure relates to a system for monitoring post-translational modification of protein using bio-sensor with gap and manufacturing method for bio-sensor.

2. Description of the Related Art

The number of Alzheimer's patients is estimated to be 46.8 million worldwide, and the number is expected to double every 20 years, reaching about 131.5 million by 2050, with costs related with Alzheimer's estimated to be around 2 trillion dollars.

Currently, while there are some medicine that can delay the progression of the disease, no cure has been found for Alzheimer's disease. It is thus absolutely crucial that the progression rate of Alzheimer's disease is evaluated through accurate diagnosis and delayed.

The tau protein aggregation is known to be the major characteristic associated with Alzheimer's disease (AD) and various neurodegenerative diseases (referred to as "taupathies"). In healthy nerves, the tau proteins stabilize microtubules by promoting growth from the axons and neuronal polarization. In addition, pathologically, it is known that when the tau proteins are hyperphosphorylated, the tau proteins separate from microtubules to produce insoluble aggregates.

Abnormally hyperphosphorylated tau proteins and the tau protein aggregates in the brains of patients with Alzheimer's disease are observed as a source of onset, and hyperphosphorylation of the tau proteins is generally considered to be the cause of tau protein aggregation.

In addition, recent studies have shown that the hyperphosphorylation and O-glycosylation of post-translational modification (PTM) forms of the tau proteins are inversely proportional to each other.

Thus, the ability to measure the degree of hyperphosphorylation or O-glycosylation of the tau proteins may be used to determine the progression rate or prognosis of Alzheimer's disease. It can also be used to validate efficacy of new drugs in the development of the new drugs.

However, the results obtained by using quantitative analysis of not only the tau protein but also the underlying substances of disease diagnosis do not show enough correlation to diagnose the disease. This seems to be due to the individual differences of each patient, and other methods of analysis are required for accurate diagnosis rather than quantitative analysis.

PRIOR ART DOCUMENTS

Patent Literature

Korean Patent Application Laid-open No. 10-2013-0091288 (2013 Feb. 7)

Non-Patent Literature

FLEXTau: Quantification of Post-translational Modifications of Tau Protein in Vitro and in Human Disease (W. Mair et al., Anal. Chem., 2016, 88, 3704-3714)

SUMMARY

The present disclosure relates to a system for monitoring post-translational modification of protein using a biosensor with a gap, which performs with high reliability a diagnosis of a disease associated with a target protein for which impedance is measured, by measuring an impedance of a sample introduced into a sensor and calculating a change rate of the measured impedance, and to a method of manufacturing the biosensor used for the system.

According to an exemplary embodiment, a system for monitoring post-translational modification of protein may include: a sensor 100 including one or more measuring units 110 including a first electrode 140, a second electrode 160 spaced apart from the first electrode 140 by a predetermined distance to form a gap G therebetween, and an organic insulating layer 180 covering a portion of the first electrode 140 and a portion of the second electrode 160 to form an opening 117 communicating with the gap G; and a controller 200 including a power supply 220 for applying a predetermined voltage between the first electrode 140 and the second electrode 160, impedance measuring units 230 that individually measure impedances Z of at least two target measurement samples which are introduced into the sensor 100, and a calculation unit 240 that calculates a change rate of impedance $\Delta Z$ by a predetermined method based on the impedance Z measured by the impedance measuring units 230.

In one embodiment, the gap G between the first electrode 140 and the second electrode 160 may be equal to or less than 1 μm.

In one embodiment, the target substance placed in the gap G may include a first conjugate S1 including a microbead b and a first antibody 10 bound to the microbead b, a second conjugate S2 including the microbead b, the first antibody 10 bound to the microbead b, and a target protein 20 bound to the first antibody 10, and a third conjugate S3 including the microbead b, the first antibody 10 bound to the microbead b, the target protein 20 bound to the first antibody 10, and a second antibody 30 bound to a first modified part of the target protein 20.

In one embodiment, the target substance placed in the gap G may include the microbead b, the first antibody 10, which is bound to the microbead b, the target protein 20 bound to the first antibody 10, and a fourth conjugate S4 including a third antibody 40 bound to a second modified part of the target protein 20, in which an amount of the first modified part of the target protein 20 and an amount of the second modified part of the target protein 20 may be inversely proportional to each other.

In one embodiment, the impedance Z of the substance placed in the gap G may decrease as the amount and type of the substance bound to the microbead b increases.

In one embodiment, when $Z_1$ is an impedance measured when a first sample including the second conjugate S2 is introduced into the sensor 100, and $Z_2$ is an impedance measured when a second sample including the third conjugate S3 is introduced into the sensor 100, the change rate of impedance calculated by the calculation unit 240 may be calculated as $Z_1-Z_2/Z_1$.

In one embodiment, when $Z_1$ is an impedance measured when a first sample including the second conjugate S2 is introduced into the sensor 100, $Z_2$ is an impedance measured when a second sample including the third conjugate S3 is introduced into the sensor 100, and $Z_3$ is an impedance measured when a third sample including the fourth conjugate S4 is introduced into the sensor 100, the change rate of impedance $\Delta Z$ calculated by the calculation unit 240 may be calculated as $Z_1-Z_2/Z_1-Z_3$.

In one embodiment, the controller 200 may further include a database 250 for storing the change rate of impedance $\Delta Z$ calculated by the calculation unit 240, and the calculation unit 240 may further calculate comparison result data by comparing a change rate of impedance $\Delta Z_1$ calculated at a first time point and a change rate of impedance $\Delta Z_2$ calculated at a second time point after the first time point.

In one embodiment, the microbead b may be a magnetic bead, and the system may further include a magnetic body 300 for guiding the magnetic bead through the opening 117 so that the magnetic bead is placed in the gap G.

System for Monitoring Post-Translational Modification of Protein.

In one embodiment, the target protein 20 may be a tau protein.

In one embodiment, the first modified part of the target protein 20 may include a phosphorylation site, and the second modified part of the target protein 20 may include an O-glycosylation site.

In one embodiment, the second antibody 30 may be an antibody which binds to the phosphorylation site of the target protein 20 and the third antibody 40 may be an antibody which binds to the O-glycosylation site of the target protein 20.

According to an embodiment, a method for manufacturing a sensor with a nanogap is also provided, which may include forming a first metal layer on a substrate, forming a first photoresist pattern on the first metal layer, forming a first electrode by etching the first metal layer and an undercut under the first photoresist pattern, forming a second metal layer on a region where the first metal layer is removed and on the first photoresist pattern, removing the first photoresist pattern and the second metal layer disposed on the first photoresist pattern, forming a second photoresist pattern on the first electrode and on a remaining second metal layer, etching the remaining second metal layer to form a second electrode spaced apart from the first electrode by a predetermined distance, and forming an organic insulating layer covering a portion of the first electrode and a portion of the second electrode and forming an opening on a gap between the first electrode and the second electrode.

In one embodiment, the first metal layer may be formed on the inorganic insulating layer disposed on the substrate.

In one embodiment, the gap between the first electrode and the second electrode may be equal to or less than 1 μm.

According to the present disclosure, by using antibodies which are different to each other and bind to post-translationally modified parts of a target protein having an inversely proportional relationship with each other, impedances of conjugates bound thereto are respectively measured and a change rate of the measured impedances is used as an index, and accordingly, a reliable result of detection can be obtained as to increase or decrease of the target protein corresponding to the desired post-translational modification and degree of such increase or decrease.

Particularly, since the use of the change rate of impedance as an index enables to clarify the risk level or the rate of progress of the disease related with the target protein, and also clearly distinguish between the normal sample and disease sample, the disadvantage of the conventional ELISA, which is unable to provide precise diagnosis with the quantitative analysis of the target protein, is solved.

In addition, without being limited to any specific target protein, the present disclosure may be applied to any target protein that includes a first modified part and a second modified part in an inverse relationship with each other, and accordingly, there is an advantage that the present disclosure can be widely used for diagnosis of diseases associated with protein abnormality.

Further, since it is possible to measure the degree of modification of not only the post-translationally modified target proteins having inversely proportional relationship with each other, but also one post-translational modification form, there is an advantage that the present disclosure can be widely used regardless of the kind of protein.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which:

FIGS. 7A to 7C are diagram showing the results according to Verification Experiment 3;

FIGS. 10A to 10C are diagram showing the results according to Verification Experiment 6;

FIGS. 13A to 13C are diagram showing the results according to Verification Experiment 8-1;

FIGS. 14A to 14C are diagram showing the results according to Verification Experiment 8-2;

FIGS. 15A to 15C are diagram showing the results according to Verification Experiment 8-3;

FIGS. 16A to 16C are diagram showing the results according to Verification Experiment 8-4;

FIGS. 17A to 17C are diagram showing the results according to Verification Experiment 8-5;

DETAILED DESCRIPTION

Hereinafter, the present disclosure will be described in detail below with reference to the accompanying drawings.

1. System for Monitoring Post-Translational Modification of Protein

A system for monitoring post-translational modification of protein according to an exemplary embodiment will be described in great detail with reference to the FIGS. 1 to 4.

Figure 1:
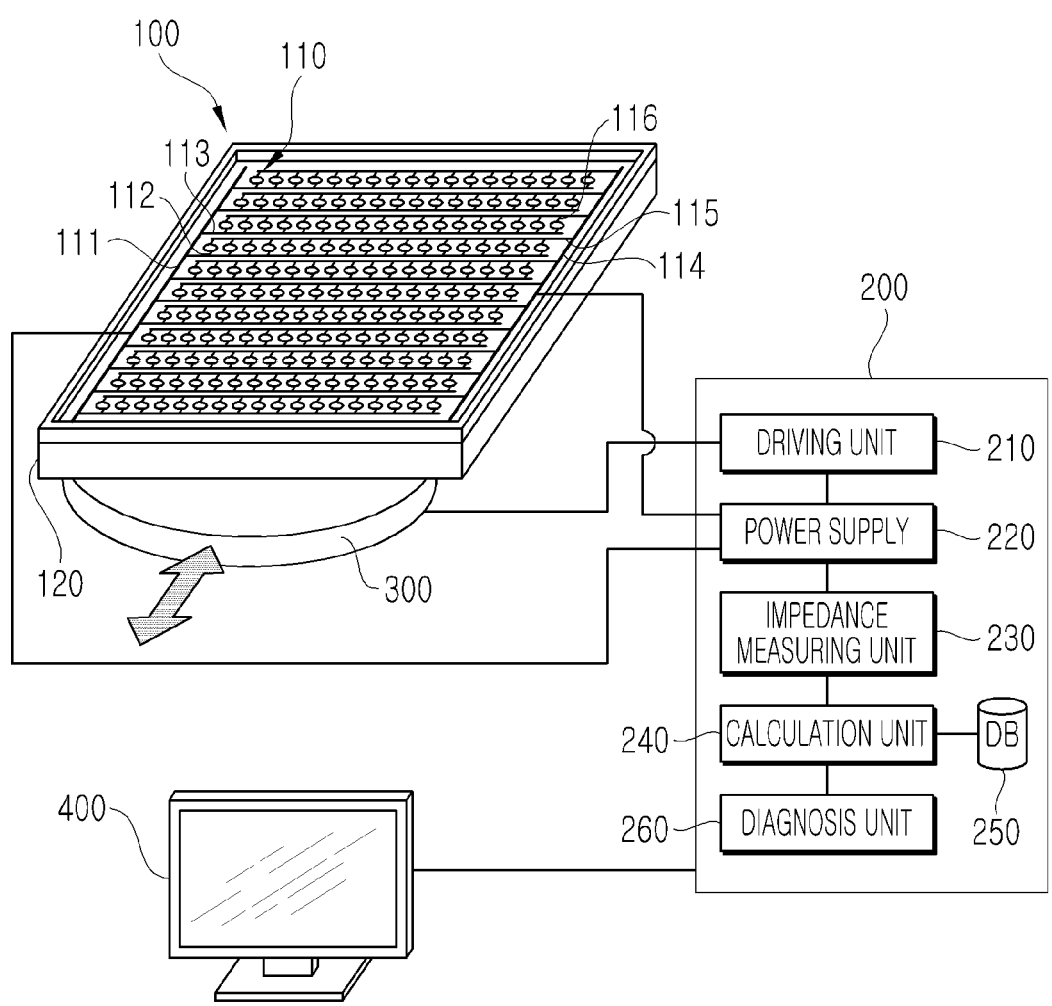
FIG. 1 is a schematic diagram provided to explain a configuration of a system for monitoring post-translational modification of protein according to an exemplary embodiment.
Figure 2:
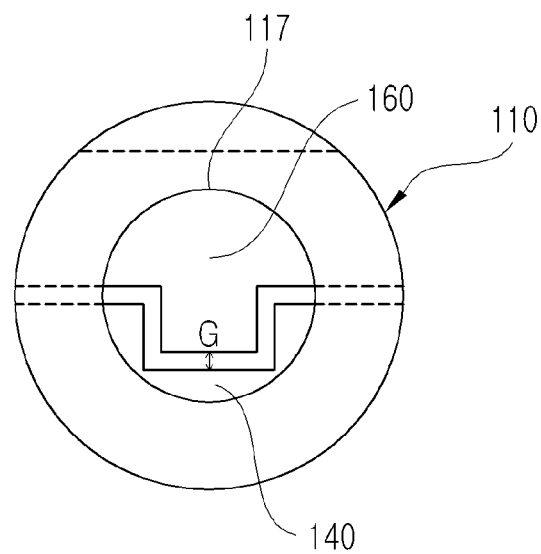
FIG. 2 is a view provided to explain the measuring unit 110 in FIG. 1.
Figure 3:
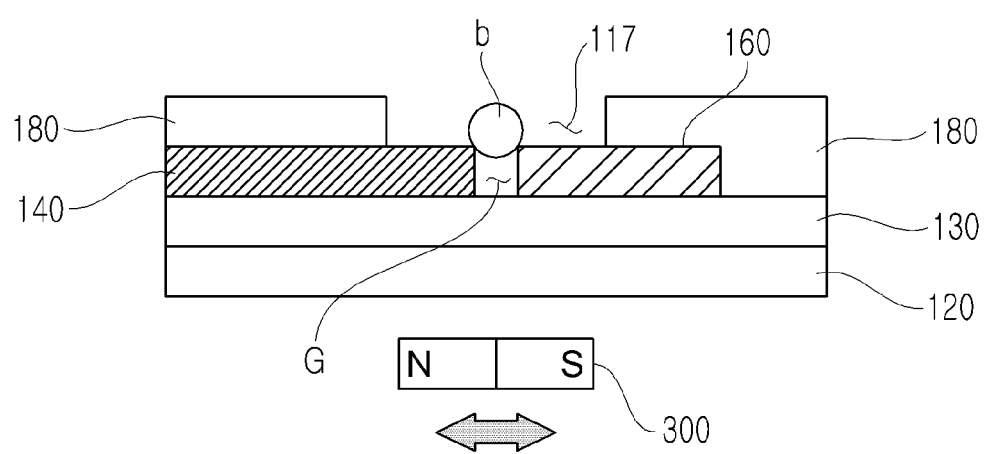
FIG. 3 is a cross-sectional view provided to explain the measuring unit 110 in FIG. 2.
Figure 4:
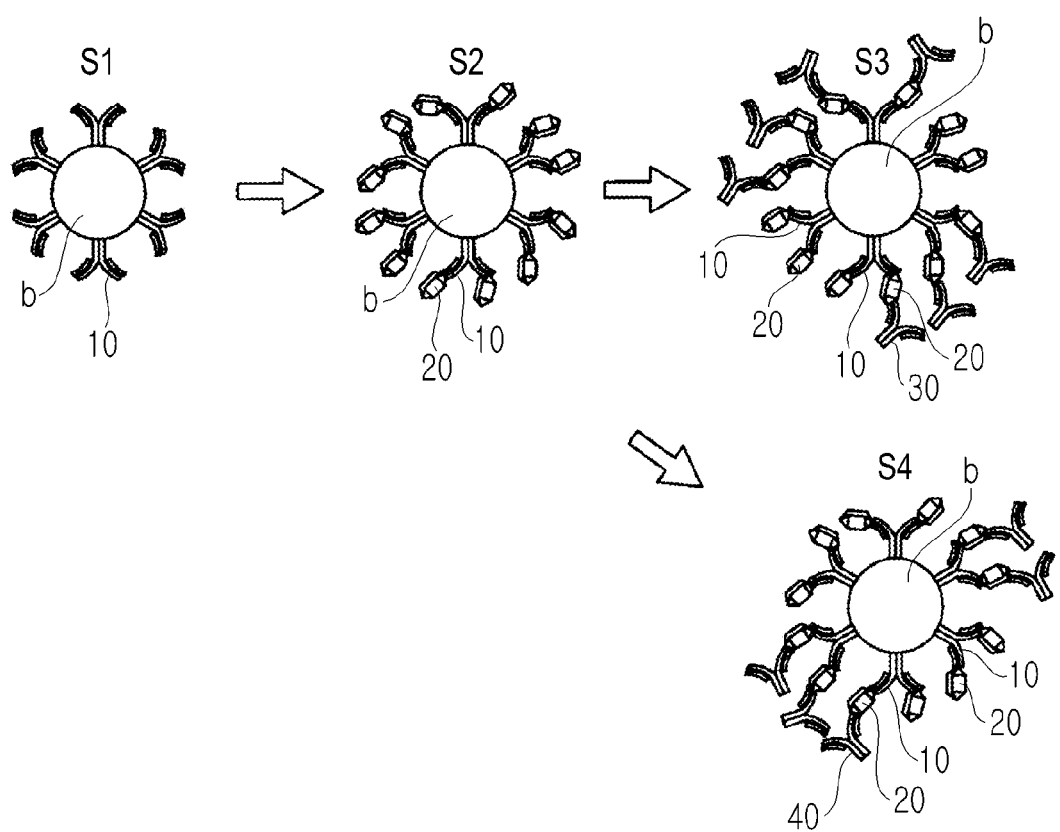
FIG. 4 is a view provided to explain a target substance of impedance measurement.

FIG. 1 is a schematic diagram provided to explain a configuration of a system for monitoring post-translational modification of protein according to an exemplary embodiment, FIG. 2 is a view provided to explain the measuring unit 110 in FIG. 1, FIG. 3 is a cross-sectional view provided to explain the measuring unit 110 in FIG. 2, and FIG. 4 is a view provided to explain a target substance of an impedance measurement.

Referring to FIG. 1, a system for monitoring post-translational modification of protein includes a sensor 100, a controller 200, a magnetic body 300, and a display 400.

The sensor 100 includes one or more measuring units 110 on which a target substance of impedance measurement is placed.

The measuring units 110 will be described in more detail with reference to FIGS. 2 and 3. FIG. 2 is a plan view of the measuring unit 110 of the sensor 100 in FIG. 1, and FIG. 3 is a sectional view of the measuring unit 110.

The measuring unit 110 includes a substrate 120, an inorganic insulating layer 130 disposed on the substrate 120, a first electrode 140 and a second electrode 160 individually disposed on the inorganic insulating layer 130 and spaced apart from each other by a predetermined distance to form a gap G therebetween, and an organic insulating layer 180 covering a portion of the first electrode 140 and a portion of the second electrode 160 to form an opening 117 communicating with the gap G.

Here, the substrate 120 may include an insulating material such as silicon, glass, quartz, polymer, and the like. More preferably, the substrate 120 may be formed of a transparent material, in which case there is an advantage that it is possible to optically confirm the presence or absence of microbead b.

The target substance is placed in the gap G between the first electrode 140 and the second electrode 160.

The target substance placed in the gap G between the first electrode 140 and the second electrode 160 will be described in more detail with reference to FIG. 4.

In order to measure the degree of post-translational modification by measuring an impedance of a target protein 20 present in the sample such as blood, plasma, serum, saliva, urine, tear, mucus, spinal fluid, or the like, a first conjugate S1, a second conjugate S2, and third conjugate S3, and a fourth conjugate S4 may be placed in the gap G.

The first conjugate S1 includes a microbead b and one or more first antibodies 10 bound to the surface of the microbead b.

Here, the microbead b may be a magnetic bead formed of a metal, a polymer, or the like. For example, diameter of the microbead b may be 1 μm to 5 μm, but is not limited thereto, and it may be 10 μm or greater depending on a target to be detected.

The first antibody 10 is an antibody that can bind to the target protein 20, and the microbead b may be tosylated, aminated, or treated on the carboxyl group so that the first antibody 10 is bound thereto. Here, the target protein 20 may be a tau protein, and the first antibody 10 may be an antibody that can bind to the tau protein, and more specifically, to a part (common part) that is not a post-translationally modified part of the target protein 20. However, the present disclosure is not limited to this, and any target proteins are applicable as long as there are two or more post-translationally modified parts in the target protein 20 and in a relationship in which an amount of one post-translationally modified part is inversely proportional to an amount of the other post-translationally modified part (i.e., in a relationship in which an increase in the amount of one post-translationally modified part leads to a decrease in the amount of the other post-translationally modified part).

In addition, it is of course possible that, in order to measure the degree of post-translational modification, the target protein 20 may be in such a form in which one or more post-translationally modified parts are present and only one of the post-translational modifications is measured.

The second conjugate S2 includes the microbead b, one or more first antibodies 10 bound to the surface of the microbead b, and target proteins 20 bound to the first antibodies 10.

The third conjugate S3 includes the microbead b, one or more first antibodies 10 bound to the surface of the microbead b, the target protein 20 bound to the first antibodies 10, and the second antibodies 30 bound to the first modified part of the target protein 20.

Here, the first modified part may be a phosphorylation site of the target protein 20, and the second antibody 30 may be any of Phospho-Tau (Ser202, Thr205) Antibody (AT8) MN1020 (Thermo Fisher), Anti-Tau (phosphor 5396) antibody [EPR2731]/ab109390 (abcam), Phospho-Tau (Ser202_Antibody, #11834) (Cell signaling), Phospho-Tau (Ser396) (PHF13) Mouse mAb, #9632 (Cell signaling), which binds to the phosphorylation site tau protein. However, the examples are not limited to those provided above, and may be any antibody that can bind to a phosphorylation site of tau protein.

The fourth conjugate S4 includes the microbead b, one or more first antibodies 10 bound to the surface of the microbead b, the target protein 20 bound to the first antibodies 10, and third antibodies 40 bound to the second modified part of the target protein 20.

Here, the second modified part may be an O-glycosylation site of the target protein 20, and the third antibody 40 is an antibody that binds to the O-glycosylation site of tau protein, such as O-GlcNAc (CTD110.6) Mouse mAB, #9875 (Cell signaling).

The gap G described above, in which the target substance is to be placed, is preferably of a size smaller than the diameter of the microbead b to receive the microbead b thereon, and the numerical value of the size may be equal to or less than 1 μm, for example. However, examples are not limited to this and the size of the gap G may be greater than the above example, depending on the microbead b applied for the impedance measurement.

The microbead b may be placed in the gap G through the opening 117 and the diameter of the opening 117 is preferably greater than the diameter of the microbead b and less than twice the diameter of the microbead b. With this configuration, it is possible to more effectively introduce one microbead b into each opening 117 (see Verification Experiment 1).

The first electrode 140 and the second electrode 160 are electrically connected to a power supply 220.

The power supply 220 applies a predetermined voltage between the first electrode 140 and the second electrode 160. Specifically, the power supply 220 can apply an alternating current voltage of 50 mVsin(w) between the first electrode 140 and the second electrode 160. That is, as the target substance is placed in the gap G, the first electrode 140, the second electrode 160, the power supply 220, and the target substance may be electrically connected to each other to form one electric circuit, and as a result, the impedance Z of the target substance can be measured by measuring the current or voltage flowing through the electric circuit. In other words, when the target substance including the microbead b is introduced through the opening 117 and placed in the gap G, with an application of the voltage to the sensor 100, the electrochemical impedance calculated by a predetermined method is measured.

The sensor 100 will be described again with reference to FIG. 1.

The sensor 100 includes a plurality of measuring units 110 described above, and each measuring unit 110 is connected to a first longitudinal main wire 111 and a second longitudinal main wire 114 which are applied with a predetermined voltage by the power supply 200.

The first longitudinal main wire 111 and the second longitudinal main wire 114 may be parallel to a y axis of the sensor 100.

The first longitudinal main wire 111 is connected to a plurality of first transverse main wires 112 that are branched from the first longitudinal main wire 111 and parallel to an x axis direction of the sensor 100, and the plurality of first transverse main wires 112 are connected to a plurality of first longitudinal sub wires 113 that are branched again therefrom and parallel to the y axis direction of the sensor 100. The first longitudinal sub wires 113 are electrically connected to the first electrode 140 of the measuring unit 110.

The second longitudinal main wire 114 is connected to a plurality of second transverse main wires 115 that are branched from the second longitudinal main wire 114 and parallel to the x axis direction of the sensor 100, and the plurality of second transverse main wires 115 are connected to a plurality of second longitudinal sub wires 116 that are branched again therefrom and parallel to the y axis direction of the sensor 100. The second longitudinal sub wire 116 is electrically connected to the second electrode 160 of the measuring unit 110.

That is, the voltage by the power supply 220 may be applied to the electrodes 140 and 160 of all the measuring units 110 included in the sensor 100 by the wires 111, 112, 113, 114, 115 and 116 described above.

A magnetic body 300 is provided under the sensor 100 to guide the microbead b to the opening 117 formed in each measuring unit 110. The magnetic body 300 may be an object having magnetism, such as a permanent magnet or an electromagnet. Meanwhile, it is preferable that the microbeads b are provided in the form of magnetic beads that can be moved by the attraction force according to a movement of the magnetic body 300.

The controller 200 controls the voltage applied to the sensor 100, measures the impedance of the target substance placed in the gap G, and controls the driving of the magnetic body 300.

Referring to FIG. 1, the controller 200 includes a driving unit 210, the power supply 220, an impedance measuring unit 230, a calculation unit 240, a database 250, and a diagnosis unit 260.

The driving unit 210 is electrically connected to the magnetic body 300 to control the movement of the magnetic body 300. Specifically, the driving unit 210 may control the movement of the magnetic body 300 so that the microbead b, which is the magnetic bead, is introduced into the opening 117.

The power supply 220 is a part where a predetermined voltage is applied to wires that are electrically connected thereto. Particularly, a predetermined voltage, specifically, a voltage of 50 mVsin(w) can be applied to the wires.

When the target substance is placed in the gap G between the first electrode 140 and the second electrode 160 and the power supply 220 applies a voltage, a voltage corresponding to the voltage applied by the power supply 220 is applied to the gap G.

The impedance measuring unit 230 measures the impedance Z of the target substance placed in the gap G. When it is assumed that the power supply 220 and the sensor 100 are electrically connected to each other to form one electric circuit, the impedance measuring method may adopt a method of dividing a value of the voltage applied to the electrodes 140 and 160 by a value of the current flowing through the electric circuit.

The calculation unit 240 calculates the change rate of impedance $\Delta Z$ with a predetermined method, based on the impedance Z measured by the impedance measuring unit 230.

Among a variety of applicable methods for calculating the change rate of impedance $\Delta Z$, an example method may calculate the change rate of impedance $\Delta Z$ by $Z_1-Z_2/Z_1-Z_3$ (Taumeter), where $Z_1$ is an impedance measured when the first sample including the second conjugate S2 is introduced into the sensor 100, $Z_2$ is an impedance measured when a second sample including the third conjugate S3 is introduced into the sensor 100, and $Z_3$ is an impedance measured when a third sample including the fourth conjugate S4 is introduced into the sensor 100. This is based on the fact that the amount of the first modified part of the target protein 20 and the amount of the second modified part of the target protein 20 are inversely proportional to each other, and the mathematical expression described above has an advantage that it is possible to more accurately diagnose the disease associated with the target protein 20 by considering all the change amount of the first modified part and the second modified part.

The database 250 stores the change rate of impedance $\Delta Z$ calculated by the calculation unit 240. That is, the change rate of impedance $\Delta Z$ at a first time point calculated by the calculation unit 240 is stored in the database 250, and the change rate of impedance $\Delta Z$ is re-calculated from the sample acquired from the same object at a second time point after the first point in time, so that the data at two points in time can be compared. That is, since the data is stored each time the sample is acquired, it is possible to continuously monitor the rate of the disease progress and the like by comparing the data.

The diagnosis unit 260 calculates information of the disease associated with the target protein 20 that is the target of the impedance measurement, such as a risk level, a rate of progress of the disease, or the like, using the change rate of impedance ΔZ. For example, the higher change rate of impedance ΔZ can be calculated as indicating a higher risk of Alzheimer's disease, and the rates of change of the impedance ΔZ at the first and second time points may be compared to calculate the rate of progress of the Alzheimer's disease.

Measuring the impedance, calculating the change rate of impedance, and calculating information of the disease associated with the target protein 20 can be performed by computer.

The display 400 may be implemented as a monitor or the like, and this is where the information calculated by the controller 200 is output.

2. Verification Experiment 2-1. Preparation of the First Conjugate S1 (Microbead+ First Antibody)

The tosylated magnetic beads (Thermo Fisher, Dynabead M-280, 2.8 μm in diameter, 14203) and tau protein binding antibody (abcam, Anti-Tau (Phosphor S262) antibody, ab64193, 50 μl/250 μl) in 0.1M PBS buffer were incubated in an incubator at 37° C. on a roll mixer for 24 hours.

Next, the magnetic beads bound to the tau protein binding antibody were washed with 0.4% Block ACE (AbD serotec, USA) and blocked with 0.2 M Tris buffer. 30 mg/mL of the magnetic bead solution in PBST (Phosphate Buffered Saline with Tween-20, 0.01% Tween-20) containing 0.4% Block Ace was stored.

2-2. Preparation of the Second Conjugate S2 (Microbead+ First Antibody+Target Protein)

Tau protein at a concentration of 5250 ng/mL was diluted ⅟₁₀ at various concentrations (0.5 fg/mL to 50 pg/mL) with 0.1% PBST and treated with Thiamet G treatment inhibiting O-GlcNAcase or BZX2 promoting O-GlcNAcase as needed.

The magnetic beads bound to the tau protein binding antibodies were diluted to 300 μl/ml with 0.1% PBST, and then the tau protein (diluent) and the magnetic beads (diluent) were mixed at a concentration of 1:2 and reacted in the refrigerator for 22 hours.

Next, the magnetic beads bound to tau protein were washed twice with 0.1% PBST and washed twice with phosphate buffered saline (PBS), and then diluted with PBS to a magnetic bead concentration of 60 μl/ml.

2-3. Third Conjugate S3 (Microbead+First Antibody+ Target Protein+Second Antibody)

300 μl/ml of magnetic beads bound to the tau proteins were prepared in the same manner as in 2-2.

The magnetic beads were mixed with 10 ng of a second antibody (Thermo Fisher, Phospho-Tau (Ser202, Thr205) Antibody (AT8), MN1020) that can bind to the phosphorylation site of the tau protein and reacted in the refrigerator for 22 hours.

The magnetic beads bound to the second antibody were washed twice with 0.1% PBST, washed twice with PBS, and then diluted with PBS to a bead concentration of 60 μl/ml.

2-4. Fourth Conjugate S4 (Microbead+First Antibody+ Target Protein+Third Antibody)

300 μl/ml of magnetic beads bound to the tau proteins were prepared in the same manner as in 2-2.

The magnetic beads were mixed with 10.4 ng of a third antibody (Cell signaling, O-GlcNAc (CTD110.6) Mouse mAB, #9875) that can bind to the O-glycosylation site of tau protein and reacted in the refrigerator for 22 hours.

The magnetic beads bound to the third antibody were washed twice with 0.1% PBST, washed twice with PBS, and then diluted with PBS to a magnetic bead concentration of 60 μℓ/ml.

2-5. Verification Experiment 1

Figure 5:
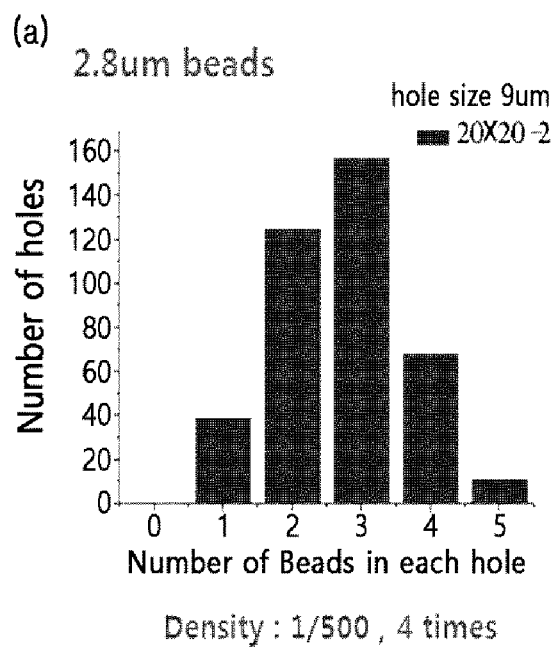
FIG. 5 is a diagram showing the results according to Verification Experiment 1.
Figure 5:
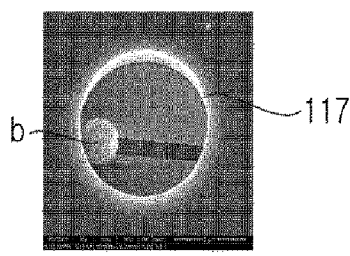
Figure 5:
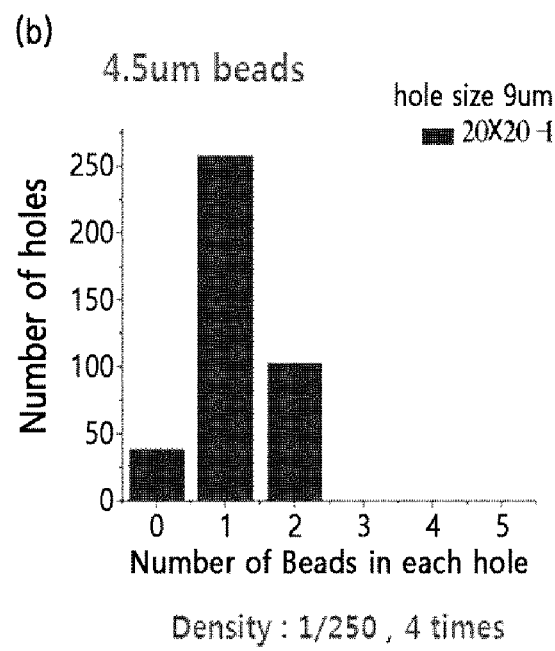
Figure 5:
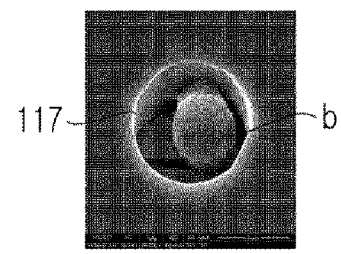

The verification experiment was conducted to find a diameter that allows one microbead b to be introduced into one opening 117 with high efficiency (FIG. 5) in a system for monitoring post-translational modification of protein according to an embodiment of the present disclosure.

In the sensor 100 having a 20×20 array, each of the openings 117 was formed in a diameter of 9 μm, into which (a) microbead b having a diameter of 2.8 μm; and (b) microbead b having a diameter of 4.5 μm were introduced and then the number of microbeads b introduced into each opening 117 was counted.

The result of the experiment confirmed that, in (a), the distribution of the microbeads b introduced into the opening 117 was not constant, whereas in (b), none of the openings 117 had three or more micro-beads b introduced thereinto and one microbead b can be introduced into each opening 117 with a high probability.

Verification Experiment 1 confirmed that the diameter of the opening 117 is preferably greater than the diameter of the microbead b, but not more than twice the diameter of the microbead b.

2-6. Verification Experiment 2

Figure 6:
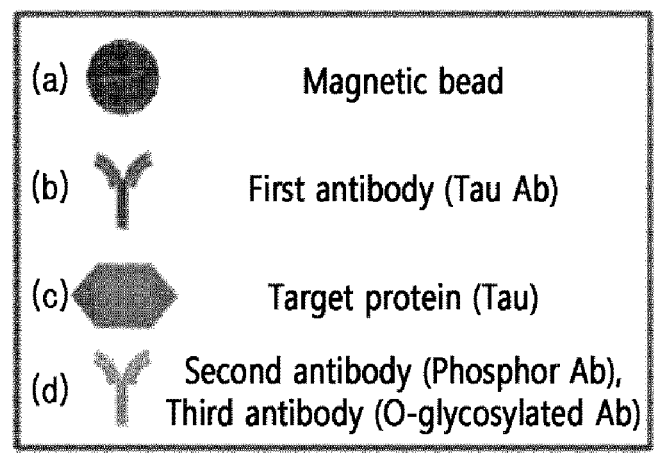
FIG. 6 is a diagram showing the results according to Verification Experiment 2.
Figure 6:
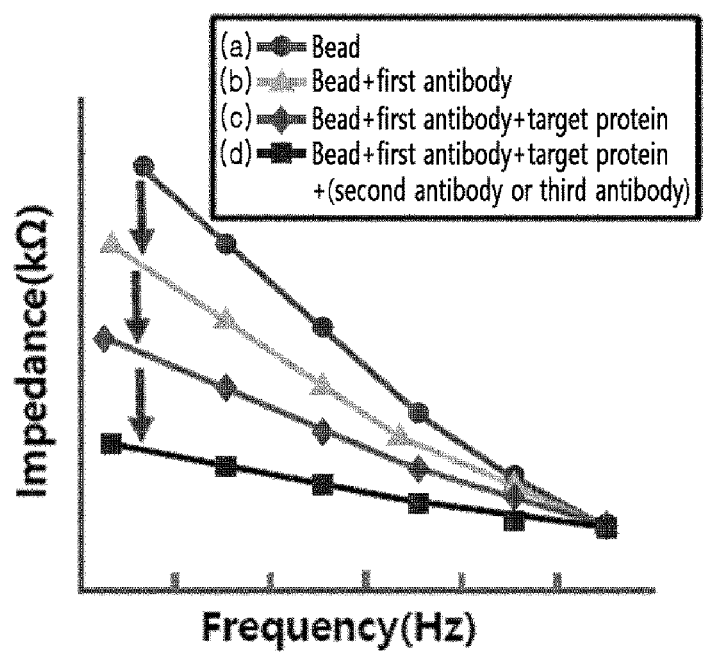

The verification experiment was conducted to investigate the tendency of the impedance Z measured as substances were additionally bound to the microbead b in the system for monitoring post-translational modification of protein according to the embodiment of the present disclosure (FIG. 6).

The impedance measurements were obtained with respect to cases where the target sample disposed in the gap G between the first electrode 140 and the second electrode 160 was: (a) the microbead b; (b) the first conjugate S1 (microbead+first antibody); (c) the second conjugate S2 (microbead+first antibody+target protein); (d) the third conjugate (microbead+first antibody+target protein+second antibody) or the fourth conjugate (microbead+first antibody+target protein+third antibody) and compared.

The result of the impedance measurement confirmed that the measured impedances tend to decrease from (a) to (d), as the first antibody 10, then the target protein 20, then the second antibody 30, then the third antibody 40, and the like are additionally bound to the microbead b.

2-7. Verification Experiment 3

Figure 7A:
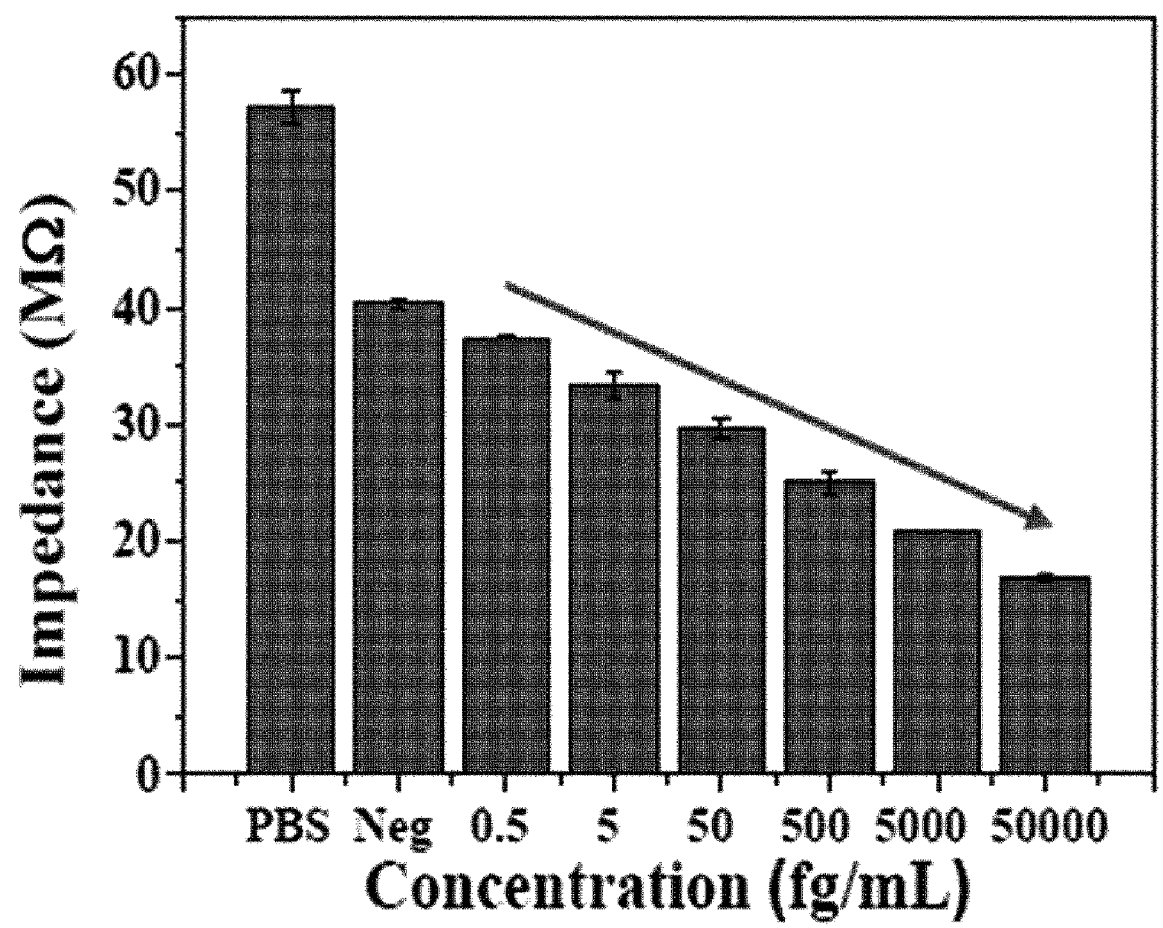
Figure 7C:
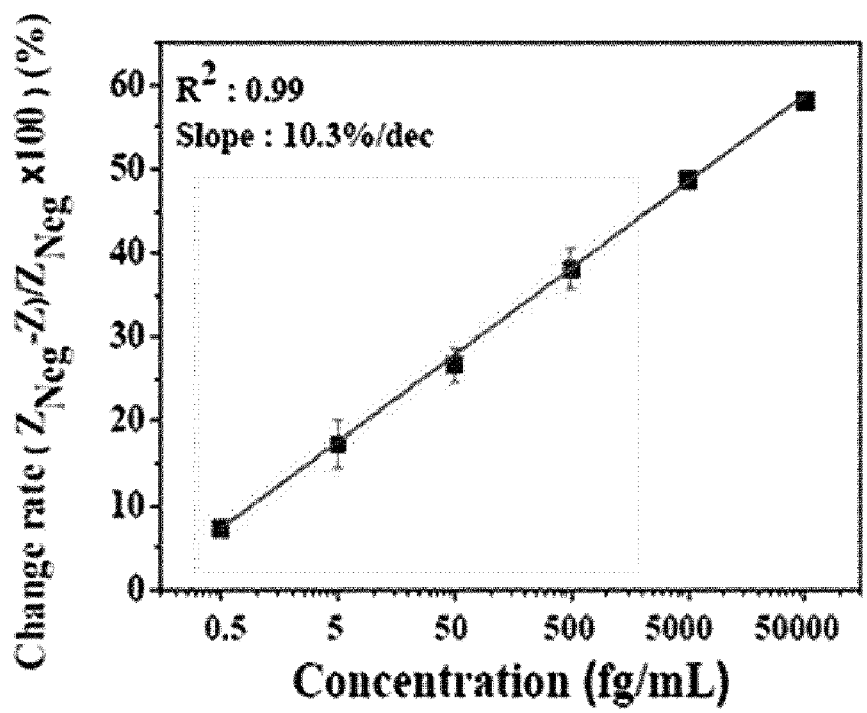

The verification experiment was conducted to verify the detection limit of the target protein 20 in the system for monitoring post-translational modification of protein according to the embodiment of the present disclosure (FIGS. 7A to 7C).

A 50 mVsin(w) voltage was applied to the sample introduced into the sensor 100, and then the impedance Z was measured at a frequency of 1 Hz, 10 Hz, and 100 Hz for respective concentrations (0.5 fg/ml, 5 fg/ml, 50 fg/ml. 500 fg/ml, 5 pg/ml, and 50 pg/ml) of the tau protein contained in the sample.

The result of measuring the impedance Z was same as the result shown in FIGS. 7A and 7B.

By 'PBS', this means that only the PBS solution that does not contain microbead b is introduced into the sensor 100, and by 'Neg', this means that the PBS solution containing the first conjugate S1 is introduced into the sensor 100, but that no tau protein is introduced.

The result of the experiment confirmed that the impedance Z decreases as the concentration of tau protein increases, i.e., as the amount of tau protein bound to the first conjugate S1 increases.

When the measured impedance in Neg is $Z_{Neg}$ and the actual measured impedance is Z, the change rate of impedance ΔZ as defined by $\Delta Z = Z_{Neg} - Z/Z_{Neg} \times 100(\%)$ was calculated, which confirmed that a meaningful change rate of impedance ΔZ appeared even when the concentration of tau protein contained in the sample was 0.5 fg/ml (FIG. 7C).

That is, the detection limit of the system for monitoring post-translational modification of protein according to the embodiment of the present disclosure was confirmed to be 0.5 fg/ml, which confirmed that detection can be achieved even with a low concentration of sample, compared with the conventional protein detection method such as Enzyme Linked Immunospecific Assay (ELISA) and digital ELISA (quanterix) that have the detection limit of 10 pg/ml and 19 fg/ml, respectively.

2-8. Verification Experiment 4

The impedance Z was measured with and without the substance that inhibits O-GlcNAcase, using the system for monitoring post-translational modification of protein according to the embodiment of the present disclosure.

A sample containing the second conjugate S2 (microbead+first antibody+tau protein) and an antibody (third antibody, O-g Antibody) that can bind to the O-glycosylation site of the tau protein was introduced into the sensor 100, and impedance Z was measured for each of the following: (a) treated with 100 μM of thiamet G which is the substance that inhibits O-GlcNAcase; and (b) thiamet G untreated, for respective concentrations (0.5 fg/ml, 5.24 fg/ml, 52.4 fg/ml and 524 fg/ml) of tau protein.

The impedance Z was measured from each sample when the first sample containing the second conjugate S2 was introduced into the sensor 100 and when the third sample containing the fourth conjugate S4 was introduced into the sensor 100.

Figure 8A:
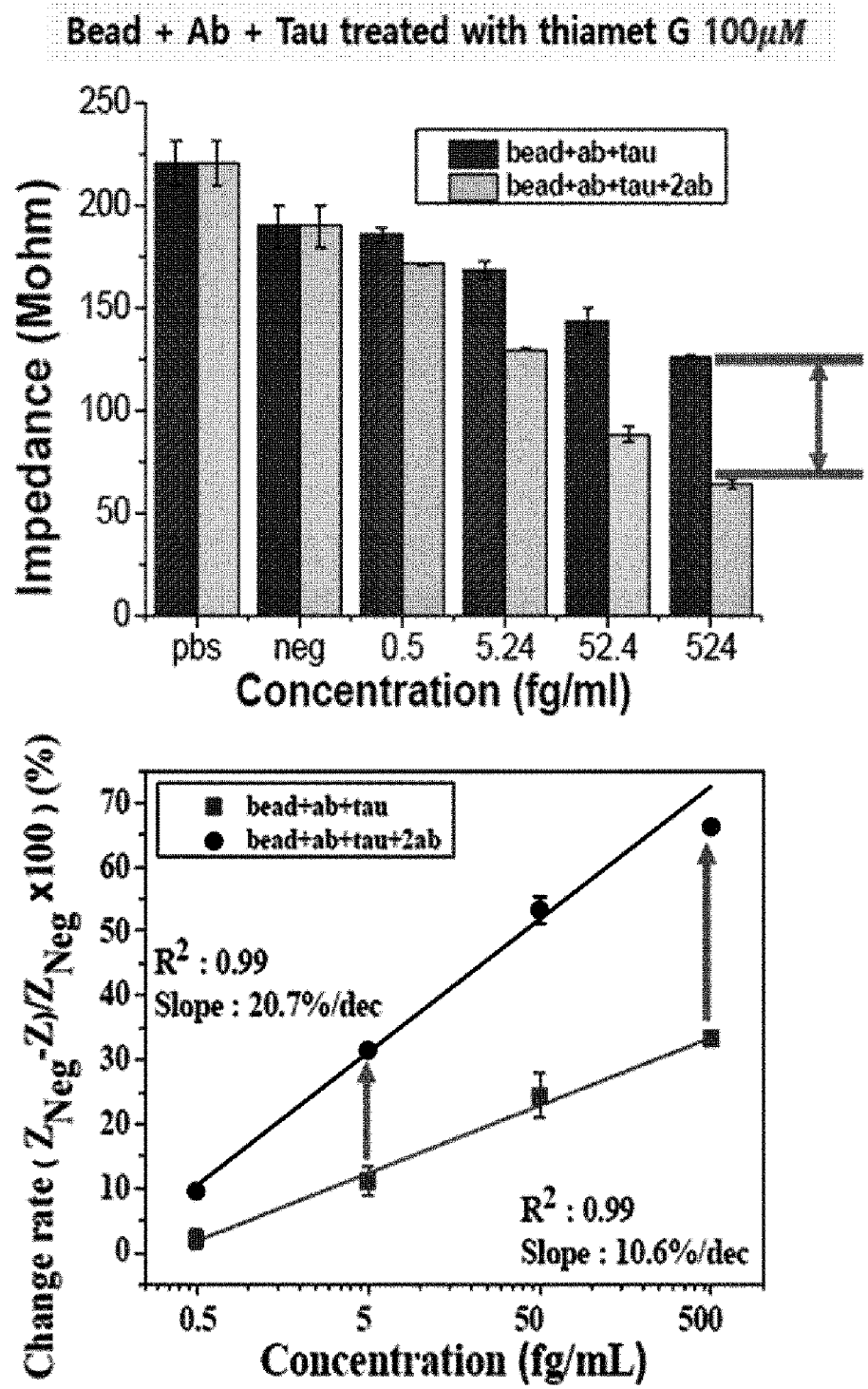
FIGS. 8A and 8B are diagram showing the results according to Verification Experiment 4.
Figure 8B:
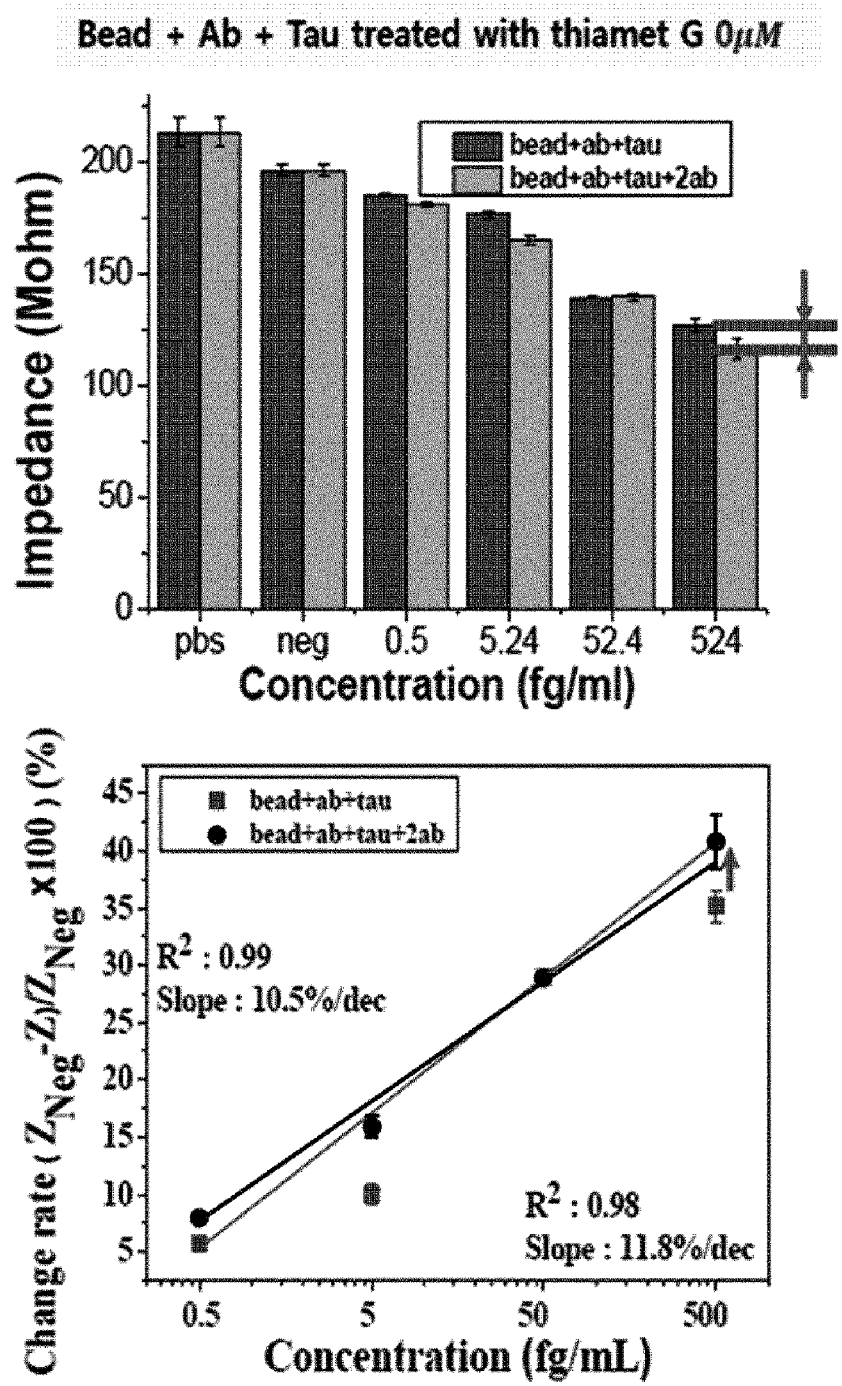

The result of the experiment was same as the result shown in FIGS. 8A and 8B.

It was confirmed that the difference in impedance ($Z_1-Z_3$) is greater when the decrease in the O-glycosylation site of the tau protein was suppressed by the treatment with thiamet G, compared to thiamet G untreated, and that the impedance difference ($Z_1-Z_3$) increases, as the concentration of tau protein increases. Particularly, it was confirmed that the difference in impedance was meaningful even at a low concentration of 0.5 fg/ml.

2-9. Verification Experiment 5

The impedance Z was measured for when treated with a substance that inhibits O-GlcNAcase; and when treated with a substance that promotes O-GlcNAcase of O-glycosylated tau protein, using the system for monitoring post-translational modification of protein according to the embodiment of the present disclosure.

A sample containing the second conjugate S2 (microbead+first antibody+tau protein) and an antibody (second antibody, AT-8 antibody) that can bind to the phosphorylation site of tau protein was introduced into the sensor 100, and impedance Z was measured for each of the following: (a) treated with 100 μM of thiamet G which is a substance that inhibits O-GlcNAcase; and (b) treated with 100 μM of BZX2 which is substance that promotes O-GloNAcase, for respective concentrations (0.5 fg/ml, 5 fg/ml, 50 fg/ml, and 500 fg/ml) of tau protein.

The impedance Z was measured from each sample when the first sample containing the second conjugate S2 was introduced into the sensor 100 and when the second sample containing the third conjugate S3 was introduced into the sensor 100.

Figure 9A:
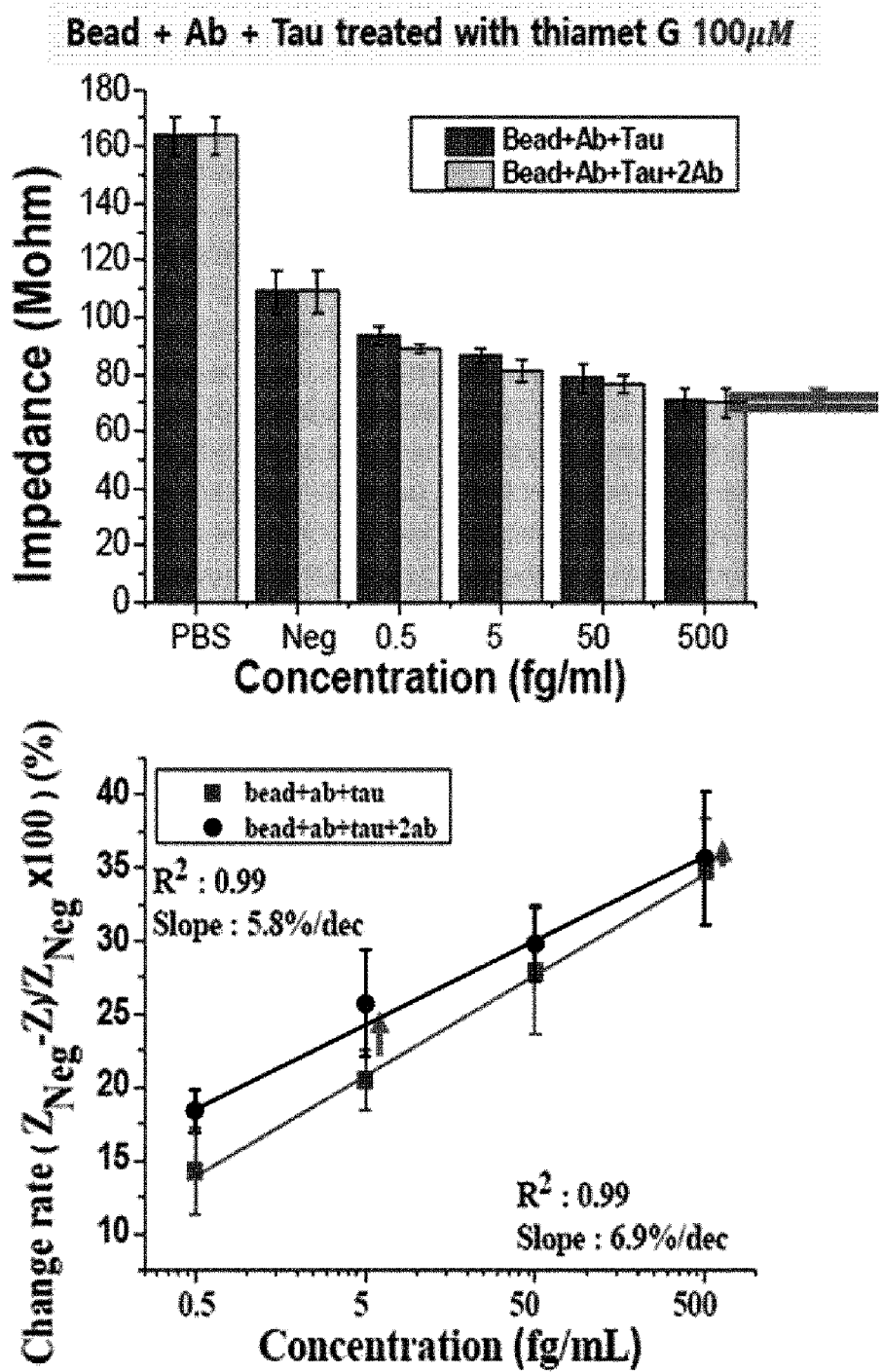
FIGS. 9A and 9B are diagram showing the results according to Verification Experiment 5.
Figure 9B:
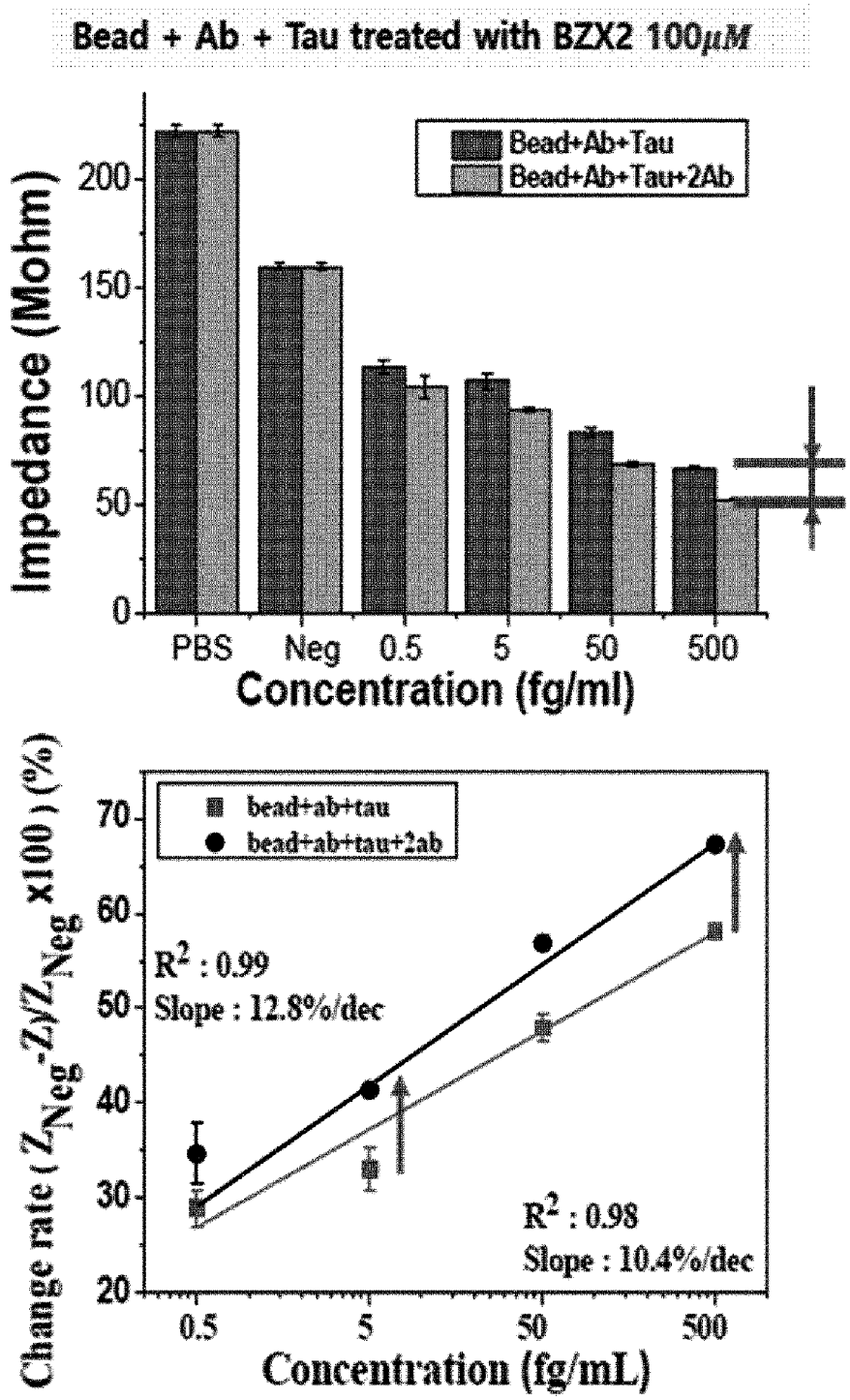

The result of the experiment was same as the result shown in FIGS. 9A and 9B.

It was confirmed that due to the inverse relationship in which the amount of the phosphorylation site of tau protein increases as the amount of the O-glycosylation site of tau protein decreases, in (b) where BZX2 is treated, the amount of the third conjugate S3 increases, and accordingly, the impedance difference ($Z_1-Z_2$) increases as the concentration of tau protein increases. Particularly, it was confirmed that the difference in impedance was meaningful even at a low concentration of 0.5 fg/ml.

2-10. Verification Experiment 6

The impedance Z was measured with and without the substance that inhibits O-GlcNAcase, using the system for monitoring post-translational modification of protein according to the embodiment of the present disclosure.

(a) 5 pg/ml of tau protein, (b) 5 pg/ml of tau protein+ second antibody (AT-8 antibody), and (c) 5 pg/ml of tau protein+third antibody (O-g Antibody) were introduced into the sensor 100, respectively, and then impedance Z was measured for PBS, Neg, Thiamet G untreated, and 100 μM of thiamet G treated samples, respectively.

Figure 10A:
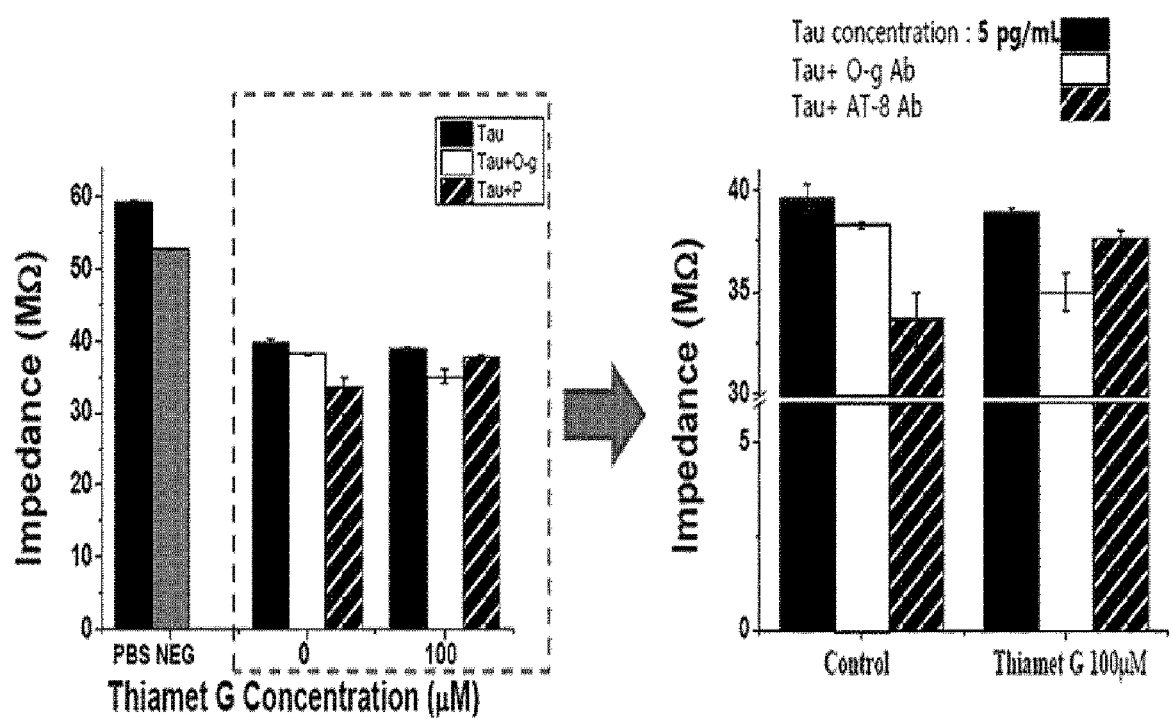
Figure 10B:
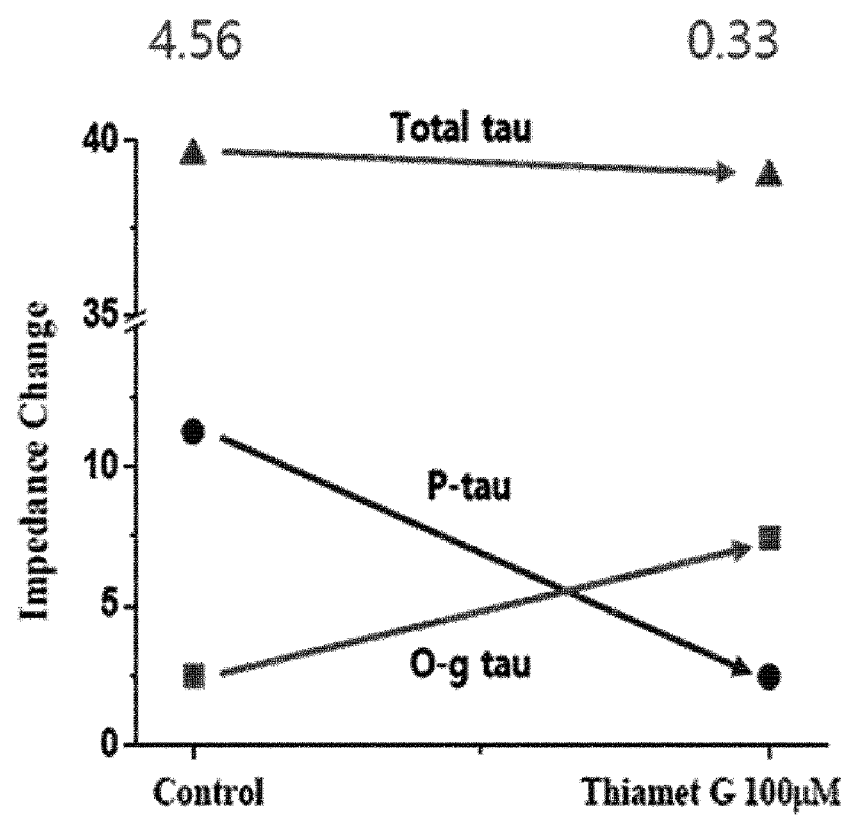

The result of the experiment was same as the result shown in FIGS. 10A to 10C.

It was confirmed that the O-glycosylation site of tau protein was increased by treating with thiamet G which inhibits the O-GloNAcase, and accordingly, (c) the impedance $Z_3$ measured as the third antibody (O-g antibody) was added decreased from 38.27 MΩ to 35.0 MΩ. In addition, it was confirmed that the phosphorylation site of tau protein decreases as the O-glycosylation site of tau protein increases, and accordingly, (b) the impedance $Z_2$ measured as the second antibody (AT-8 antibody) was added increased from 33.65 MΩ to 37.65 MΩ.

That is, it was verified that the measurement results of the impedance Z obtained through the Verification Experiment 6 for the first modified part and the second modified part, which are in inverse proportion to each other, exhibit a constant tendency that one decreases when the other increases.

2-11. Verification Experiment 7

The impedance Z was measured for a sample acquired from a control and a patient having Alzheimer's disease, using the system for monitoring post-translational modification of protein according to the exemplary embodiment.

The impedance Z was measured for: (a) sample; (b) sample+second antibody (AT-8 antibody); and (c) sample+ third antibody (O-g antibody), which were introduced into the sensor 100, respectively.

Figure 11A:
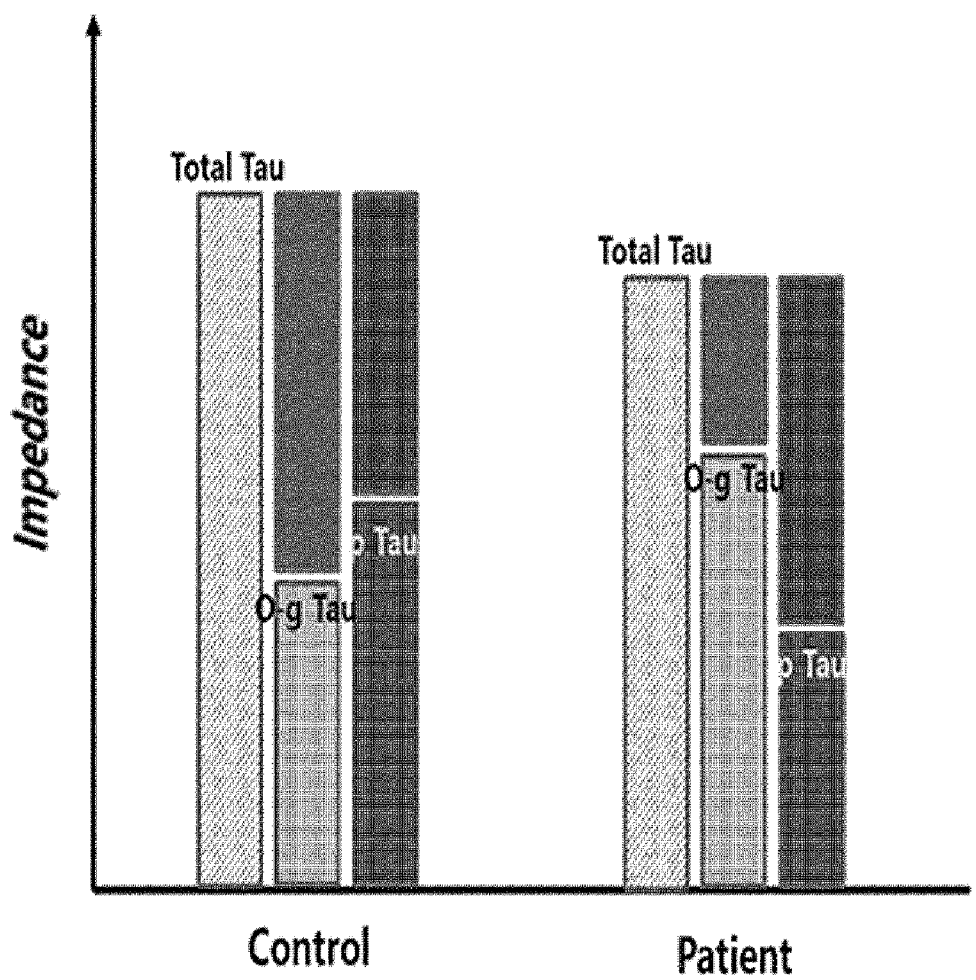
FIGS. 11A and 11B are diagram showing the results according to Verification Experiment 7.
Figure 11B:
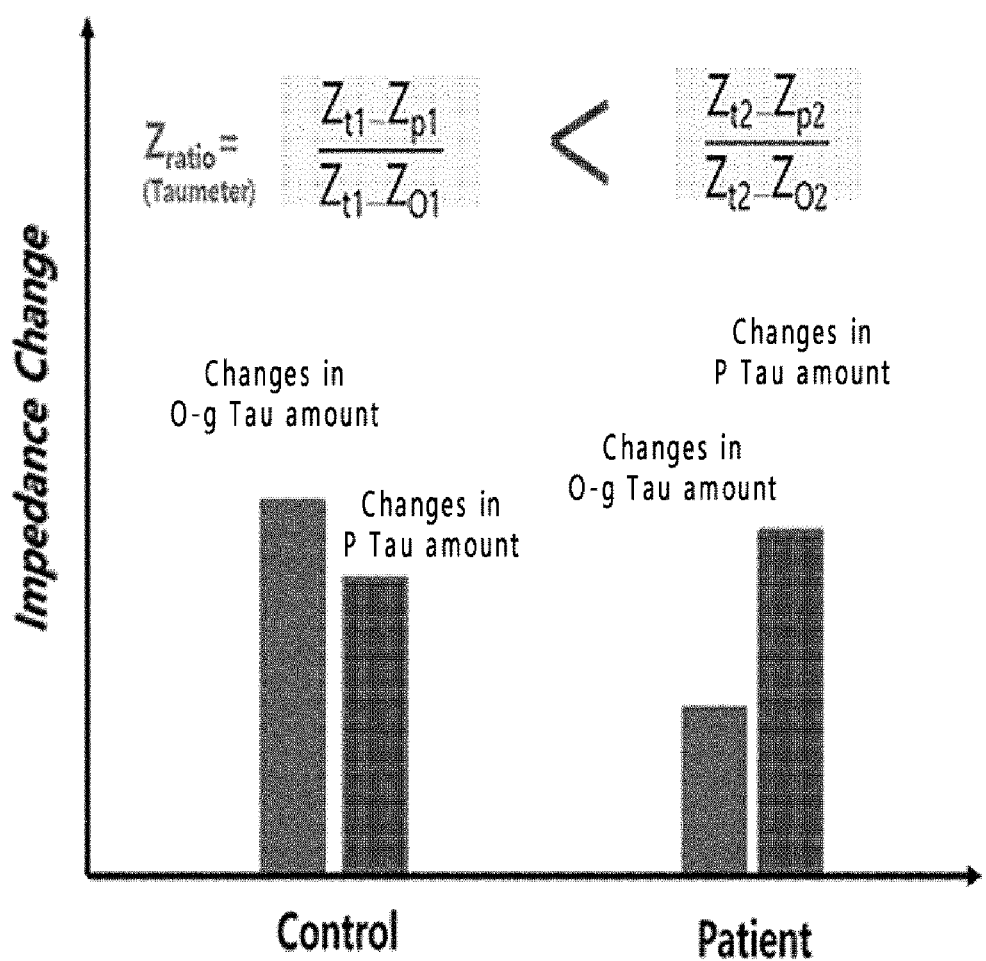

The result of the experiment was same as the result shown in FIGS. 11A and 11B.

In the patient with Alzheimer's disease who has a higher ratio of the phosphorylated tau protein contained in the sample than that of the control, it was confirmed that the impedance $Z_2$ measured in (b) was lower than that of the control.

In other words, since the patient with Alzheimer's disease has a lower ratio of the glycosylated tau protein contained in the sample than that of the control, it was confirmed that the ratio of the O-glycosylation site of tau protein contained in the sample is lower than that of the control, and accordingly, the impedance $Z_3$ measured in (c) is higher than that of the control.

Further, as a result of calculating the change rate of impedance by $\Delta Z = Z_1 - Z_2 / Z_1 - Z_3$ using the impedance $Z_1$ measured when the sample 100 alone is introduced into the sensor 100, it was confirmed that a higher change rate of impedance is shown for a patient with Alzheimer's disease.

Figure 12:
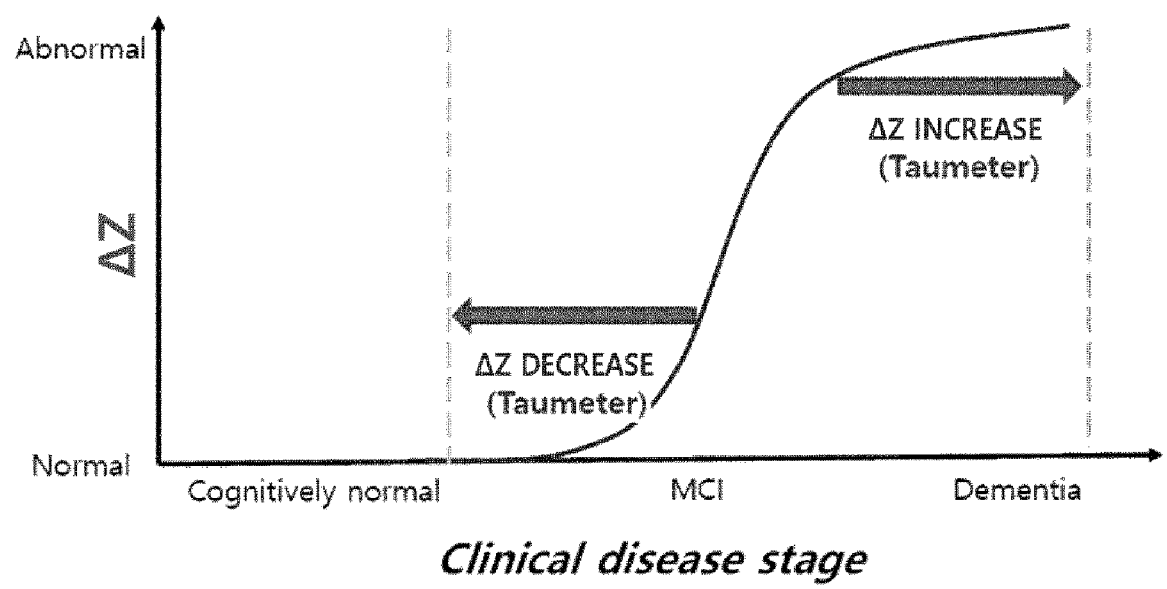
FIG. 12 is a graph showing a relationship between degrees of cognitive impairment according to a change rate of impedance.

Further, it was verified that the diagnosis of the Alzheimer's disease, and observation of the progression of the disease and the rate of the progression are enabled by using the calculated change rate of impedance ΔZ as shown in FIG. 12.

2-12. Verification Experiment 8

The experiment was conducted to verify the availability of the system for monitoring post-translational modification of protein according to the embodiments of the present disclosure for the diagnosis of Alzheimer's disease.

2-12-1. Cell Lysis (Verification Experiment 8-1)

After cell lysis, the eluted tau protein at a concentration of 5 pg/ml was introduced into the sensor 100, and impedance Z was measured for each of the following: (a) without any further sample additionally introduced into the sensor 100; (b) treated with 100 μM of thiamet G which inhibits O-GlcNAcase; and (c) treated with 100 μM of BZX2 which promotes O-GlcNAcase, after which the change rate of the impedances was calculated.

Figure 13A:
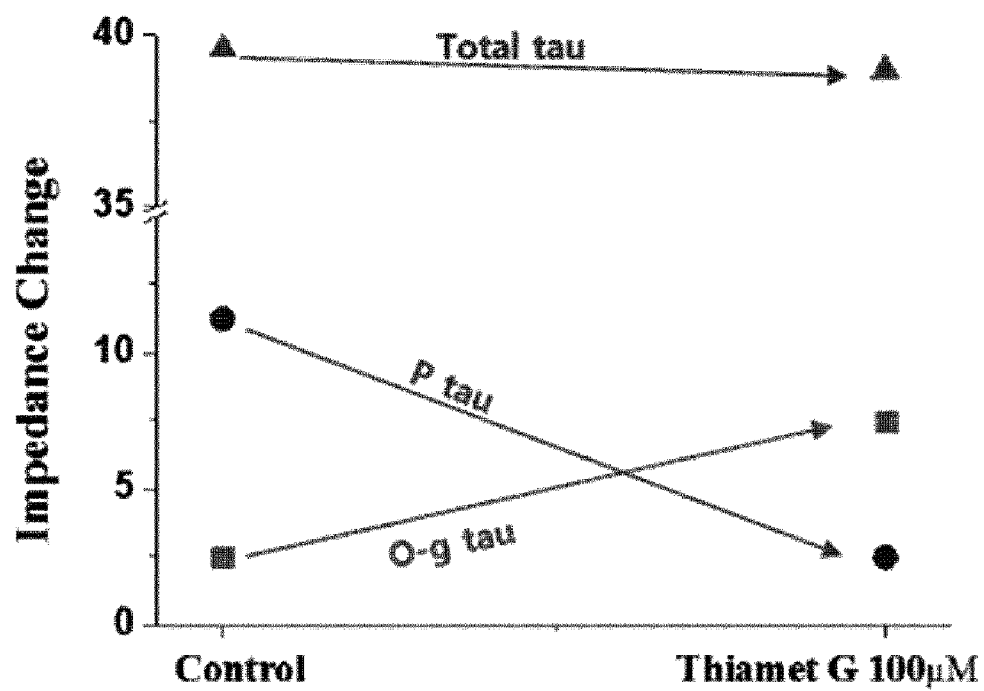
Figure 13B:
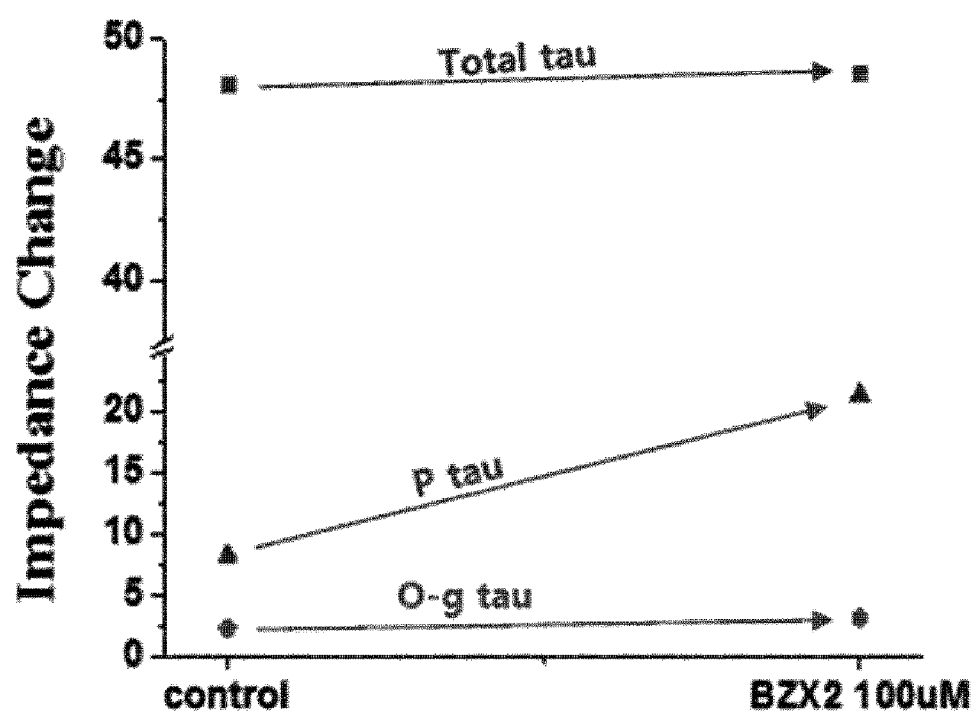

As a result, impedance $Z_1$ measured for (a) was almost unchanged, but change rate of impedance was remarkably changed according to increase or decrease of the phosphorylation site of tau protein, which verified that the increase and decrease of the phosphorylation site of tau protein and the O-glycosylation site of tau protein can be monitored by calculating the change rate of impedance (FIGS. 13A to 13C).

2-12-2. Mouse Brain Lysis (Verification Experiment 8-2)

Mouse brains from one wild type (WT) mouse (total tau protein concentration of 0.4 μg/ml) and two Alzheimer's disease transgenic (TG) mice (total tau protein concentration of 9.8 μg/ml and 20.1 μg/ml, respectively) were lysed, and the extracts thereof were diluted with PBS solution so that the total tau protein concentration was 4 pg/ml.

Each sample was introduced into the sensor 100, and the impedances $Z_1$, $Z_2$, $Z_3$ were respectively measured, and then the change rate of impedance was calculated by using the measured impendences.

Figure 14A:
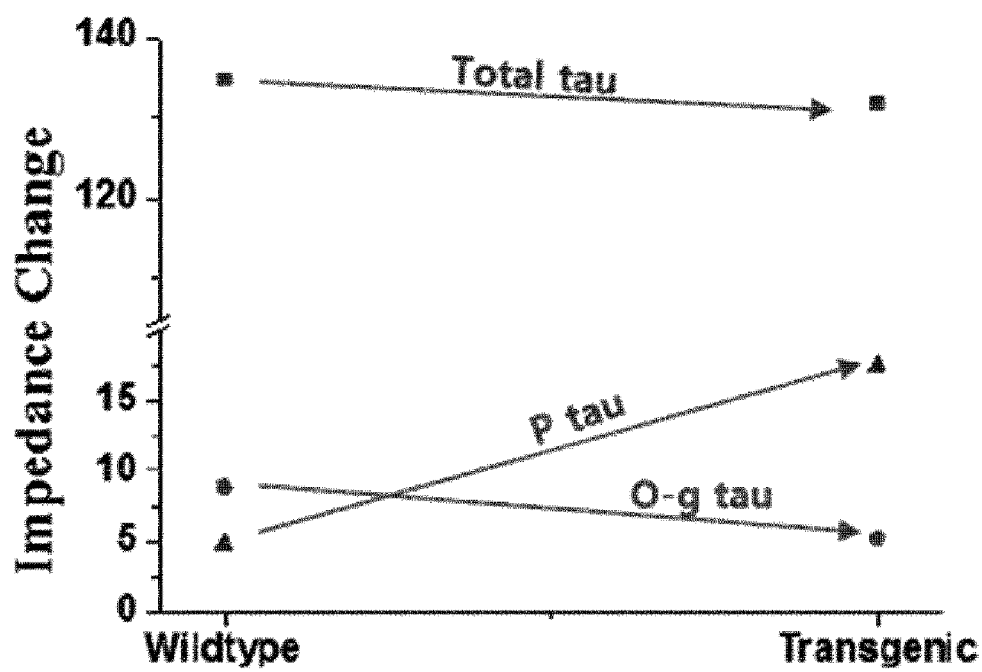
Figure 14B:
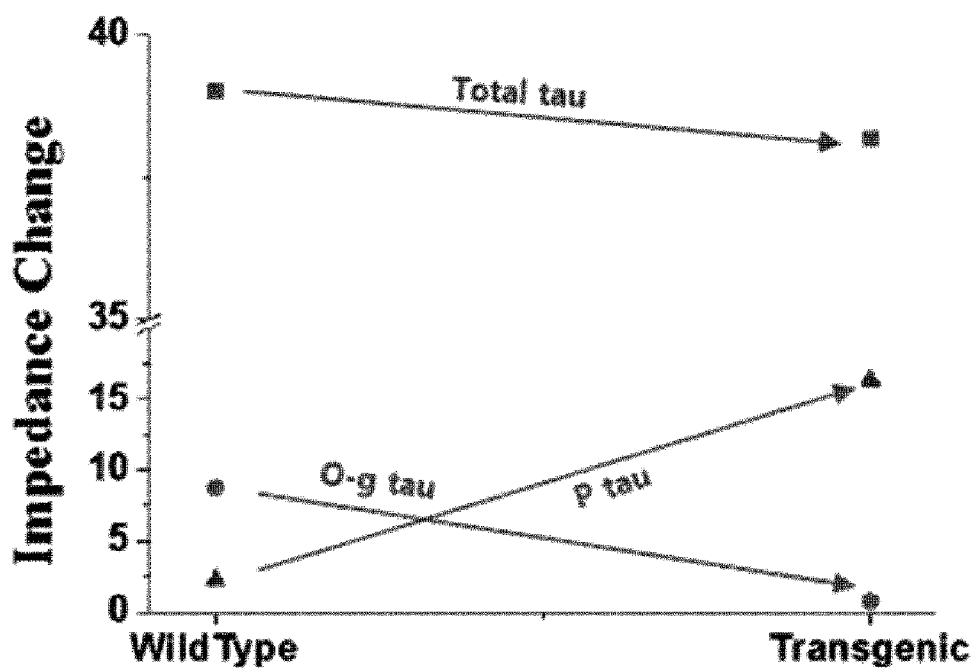

The result of the experiment verified that the difference between the wild type (WT) and the transgenic (TG) mouse can be distinguished with the change rate of impedance, and also proved that the difference between normal control and disease group can be distinguished by using the system for monitoring post-translational modification of protein according to the embodiment of the present disclosure (FIGS. 14A to 14C).

2-12-3. Mouse Blood (Validation Experiment 8-3)

Blood collected from each of a 3-month wild-type (WT) mouse (total tau protein concentration of 140.8 pg/ml), a 12-month wild-type (WT) mouse (total tau protein concentration of 193.8 pg/ml), a 3-month transgenic (TG) mouse (total tau protein concentration of 196.8 pg/ml), and a 12-month transgenic (TG) mouse (total tau protein concentration of 188.0 pg/ml) was diluted with a PBS solution to a total tau protein concentration of 14.08 pg/ml, 19.38 pg/ml, 19.68 pg/ml, and 18.80 pg/ml, respectively.

Each sample was introduced into the sensor 100, the impedances $Z_1$, $Z_2$, $Z_3$ were respectively measured, and then the change rate of impedance was calculated using the measured impedances.

The result of the experiment verified that there was almost no difference in the change rate of impedances between wild type (WT) 3-month and 12-month mice, but there was a significant difference in the impedance change ratio between transgenic (TG) mice.

Figure 15A:
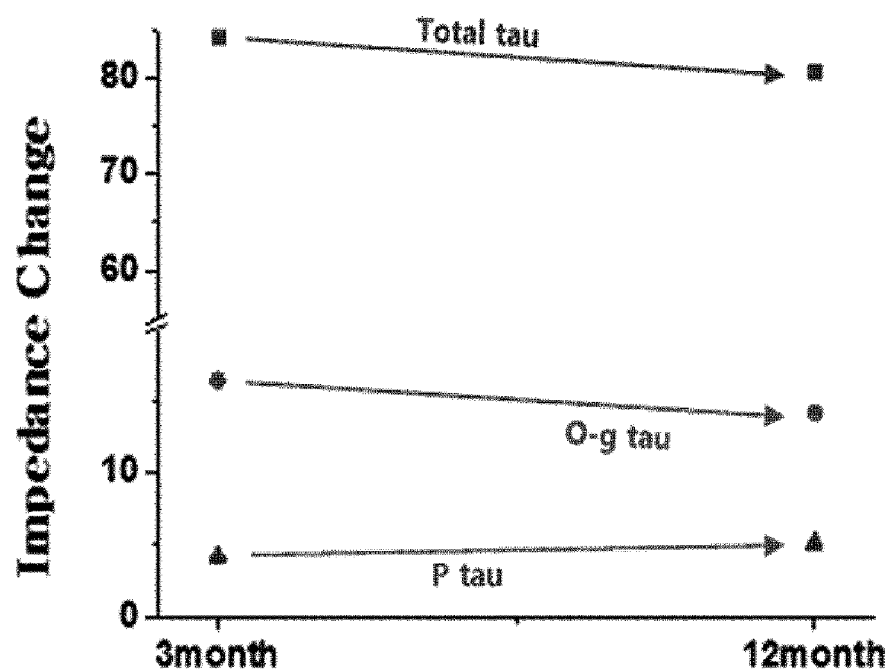
Figure 15B:
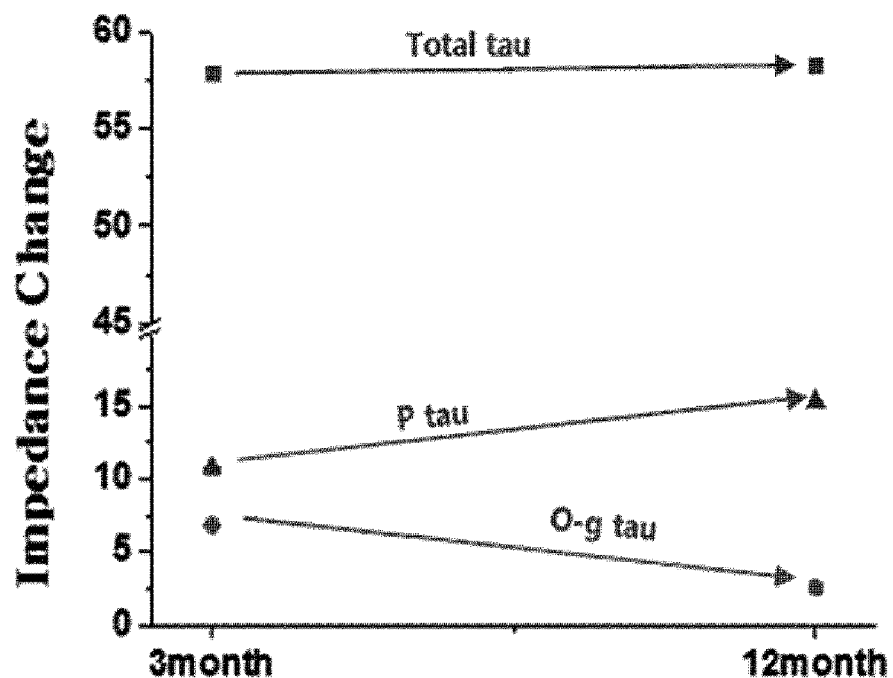

The result of the experiment verified that wild type (WT) and transgenic (TG) mice can be distinguished by the change rate of impedance, and proved that a normal mouse and a mouse having Alzheimer's disease can be distinguished by using the system for monitoring post-translational modification of protein according to the embodiment of the present disclosure (FIGS. 15A to 15C).

2-12-4. Human Blood (Normal Human Subject Vs. Human Subject with Mild Cognitive Impairment) (Verification Experiment 8-4)

Blood collected from a normal human subject and a human subject having a mild cognitive impairment (MCI) was introduced into the sensor 100 to measure respective impedances $Z_1$, $Z_2$, $Z_3$, and the change rate of impedance was calculated using the measured impedances.

Figure 16A:
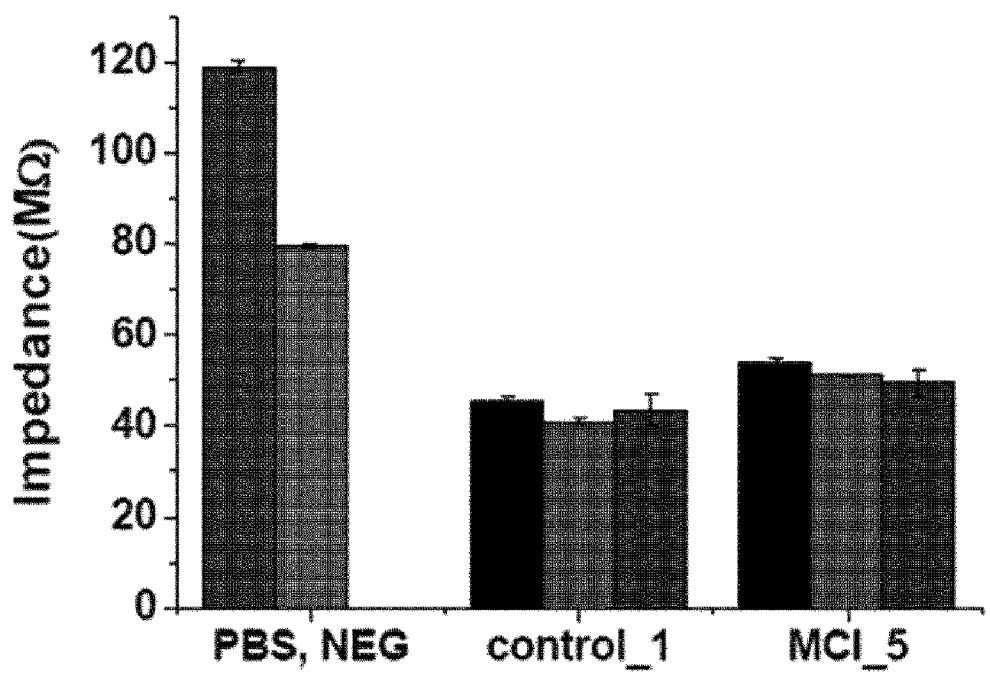
Figure 16B:
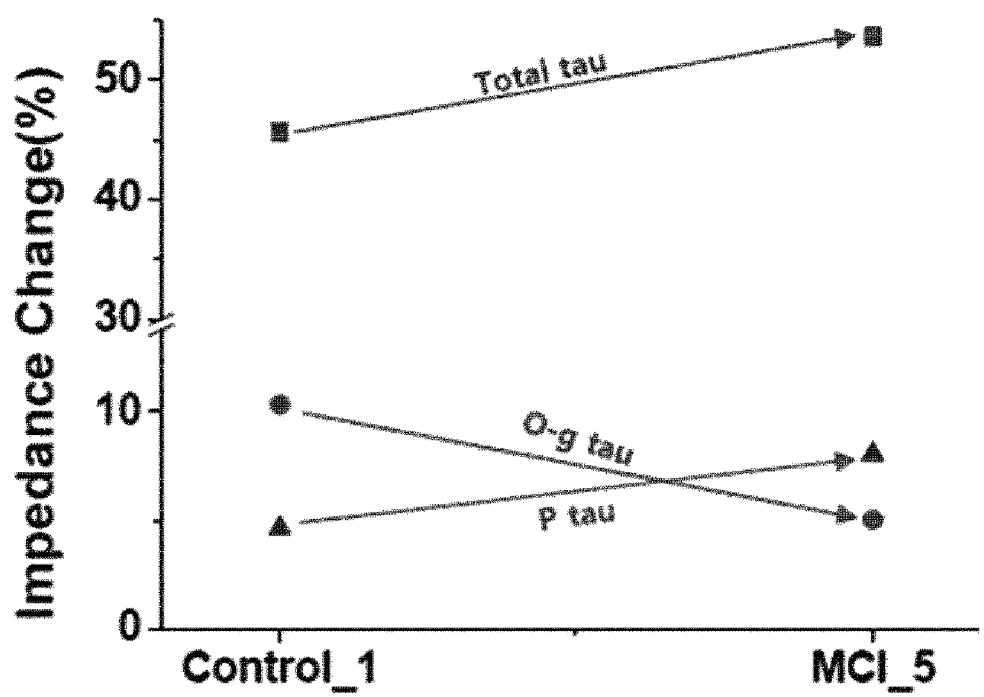

The result of the experiment was same as the result shown in FIGS. 16A to 16C.

It was confirmed that the human subject having a mild cognitive impairment (Taumeter: 1.5926, Taumeter=change rate of impedance of the phosphorylation site of tau protein/change rate of impedance of the O-glycosylation site of tau protein) showed a higher value than the normal human subject (Taumeter: 0.4468).

The result of the experiment verified that the difference between normal human subject and human subject having a mild cognitive impairment can be distinguished by calculating the Taumeter.

2-12-5. Human Blood (Normal Human Subject Vs. Human Subject with Alzheimer's Disease) (Verification Experiment 8-5)

Blood collected from a normal human subject and a human subject having Alzheimer's disease was introduced into the sensor 100 to measure respective impedances $Z_1$, $Z_2$, $Z_3$, and the change rate of impedance was calculated using the measured impedances.

Figure 17A:
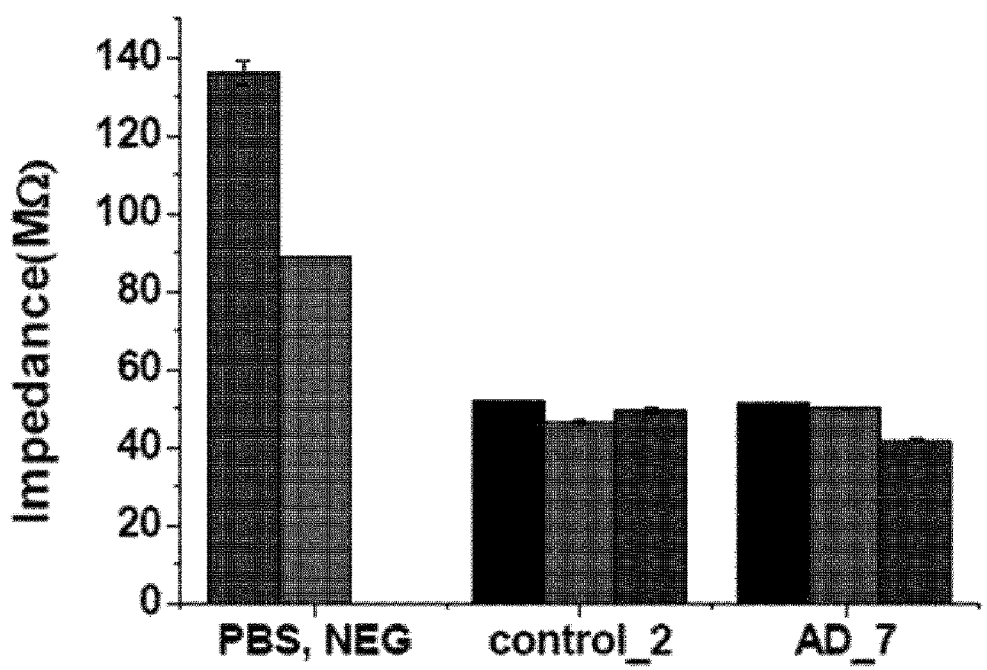
Figure 17B:
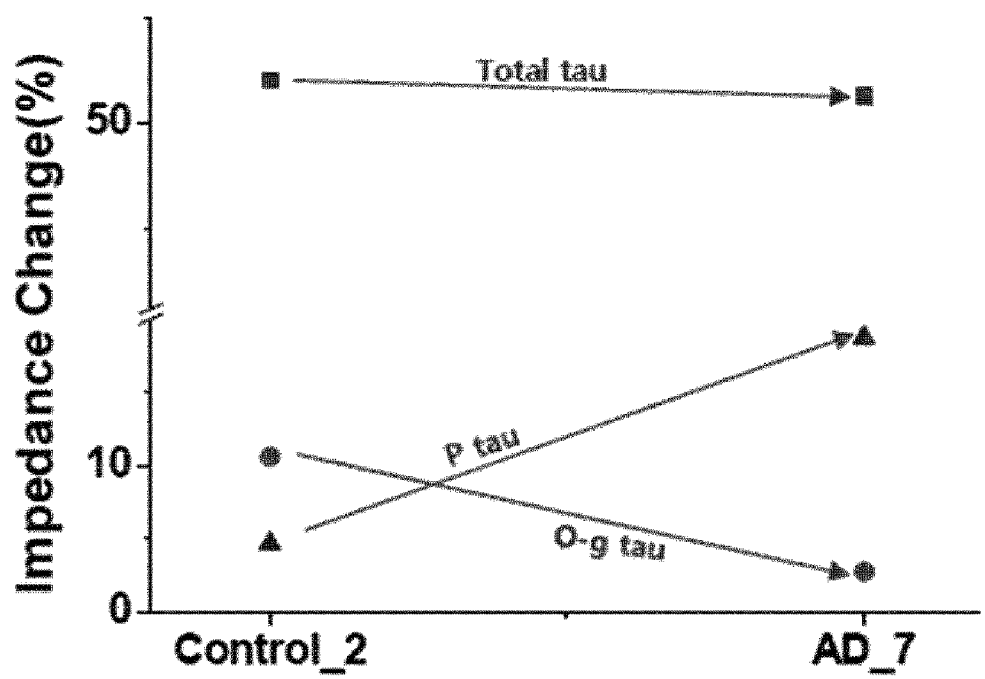
Figure 18A:
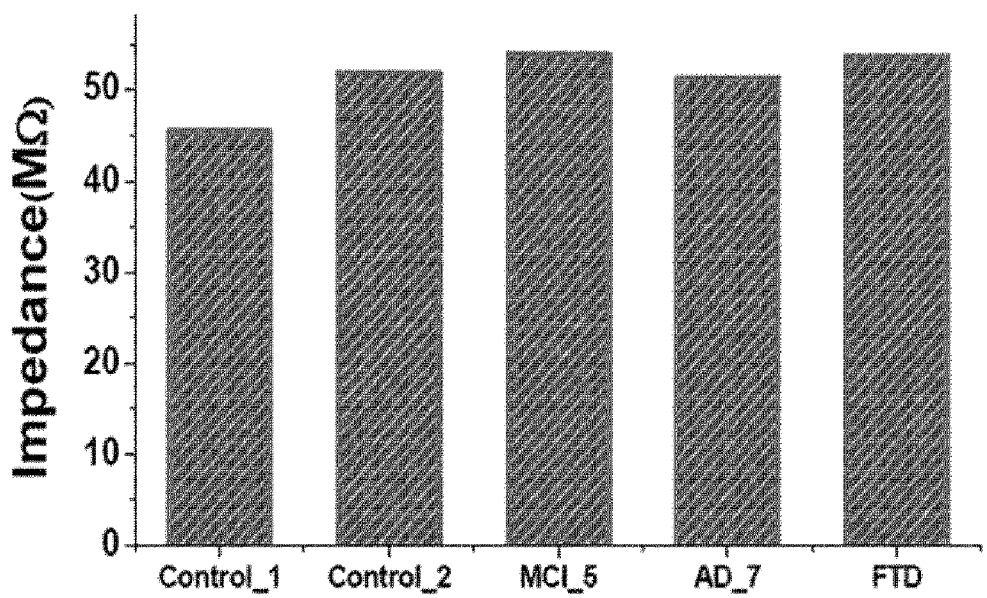
FIGS. 18A to 19B are diagrams showing the results according to Verification Experiment 9.
Figure 18B:
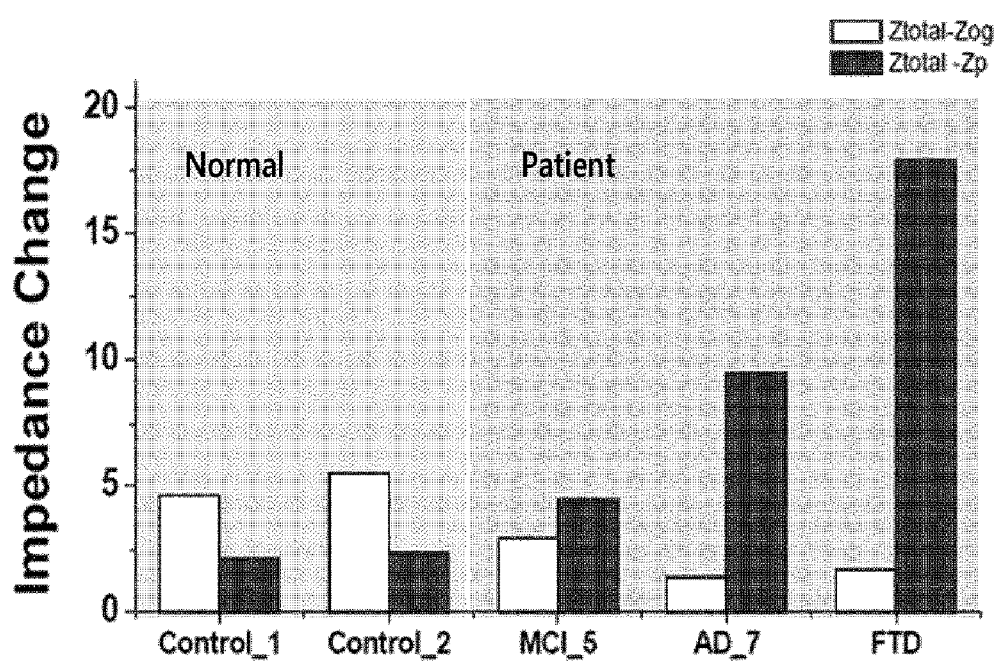
Figure 19A:
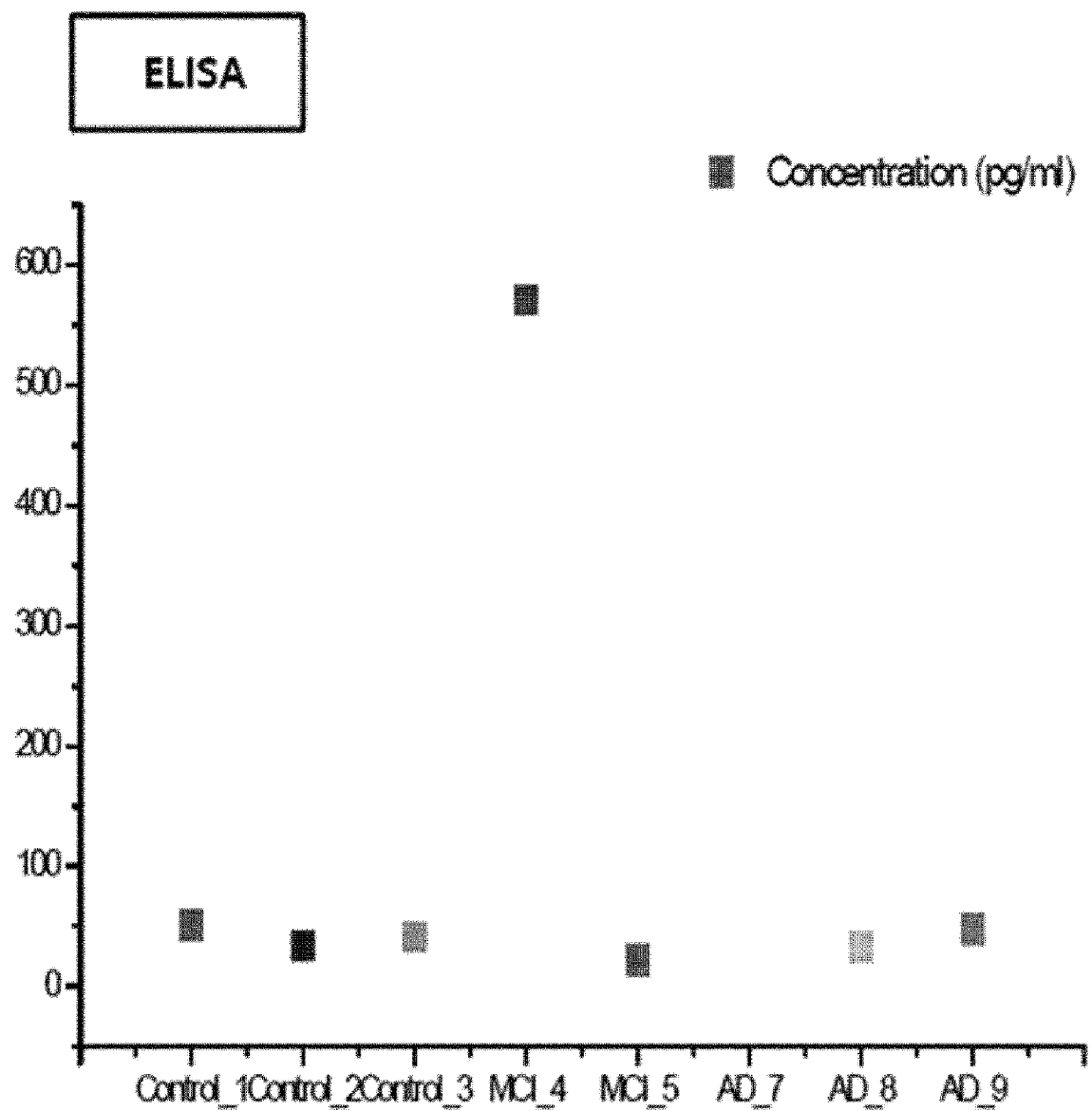
Figure 19B:
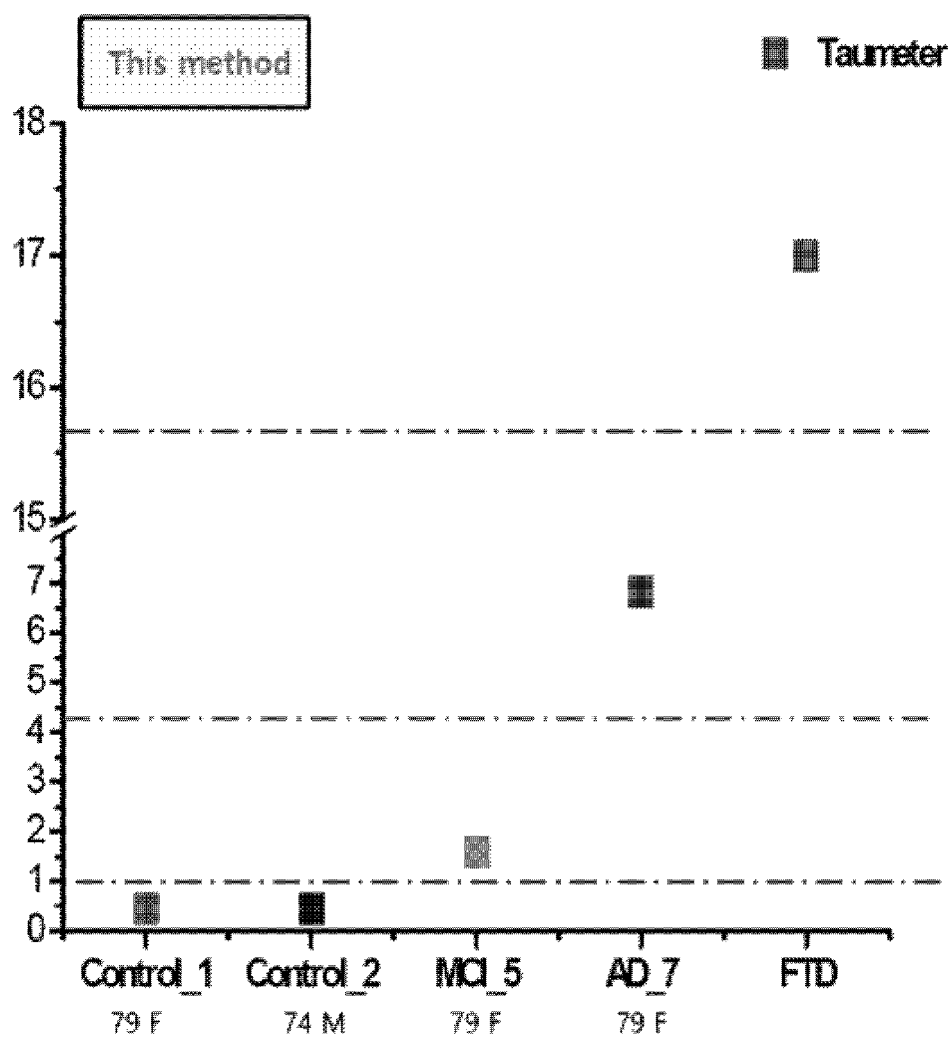

The result of the experiment was same as the result shown in FIGS. 17A to 17C.

It was confirmed that the human subject having Alzheimer's disease (Taumeter: 6.8571, Taumeter=change rate of impedance of the phosphorylation site of tau protein/change rate of impedance of the O-glycosylation site of tau protein) showed a higher value than the normal human subject (Taumeter: 0.4364).

The result of the experiment verified that the difference between normal human subject and human subject having Alzheimer's disease can be distinguished by calculating the Taumeter.

2-13. Verification Experiment 9

The experiment was conducted with blood collected from a normal human subject, a human subject having a mild cognitive impairment, a human subject having Alzheimer's disease, by (a) using ELISA, and calculating (b) change in impedance ($Z_1$–$Z_2$, $Z_1$–$Z_3$) and (c) Taumeter by using the sensor 100 according to the embodiment of the present disclosure.

The result of the experiment showed almost no change in the impedance $Z_1$ of the entire tau protein among the normal control, mild cognitive impairment subject, and Alzheimer's disease subject, and thus confirmed that it is difficult to distinguish normal human subject from the other subjects by using the method of measuring the concentration of tau protein with (a) ELISA. However, it was confirmed that the normal human subject, the human subject having a mild cognitive impairment, and the human subject having Alzheimer's disease can be clearly distinguished by using (b) impedance change and (c) Taumeter.

The result of the experiment thus confirmed that the normal human subject, the human subject having a mild cognitive impairment, and the human subject having Alzheimer's disease can be clearly distinguished by using the system for monitoring post-translational modification of protein according to the embodiment of the present disclosure (FIGS. 18A to 19B).

2-14. Verification Experiment 10

The sensitivity and specificity of the change rate of impedance ($Z_1-Z_2/Z_1$) of the phosphorylation site of tau protein (p-tau) and the change rate of impedance ($Z_1-Z_2/Z_1-Z_3$) of the phosphorylation site of tau protein and the O-glycosylation site of tau protein were confirmed.

Figure 20:
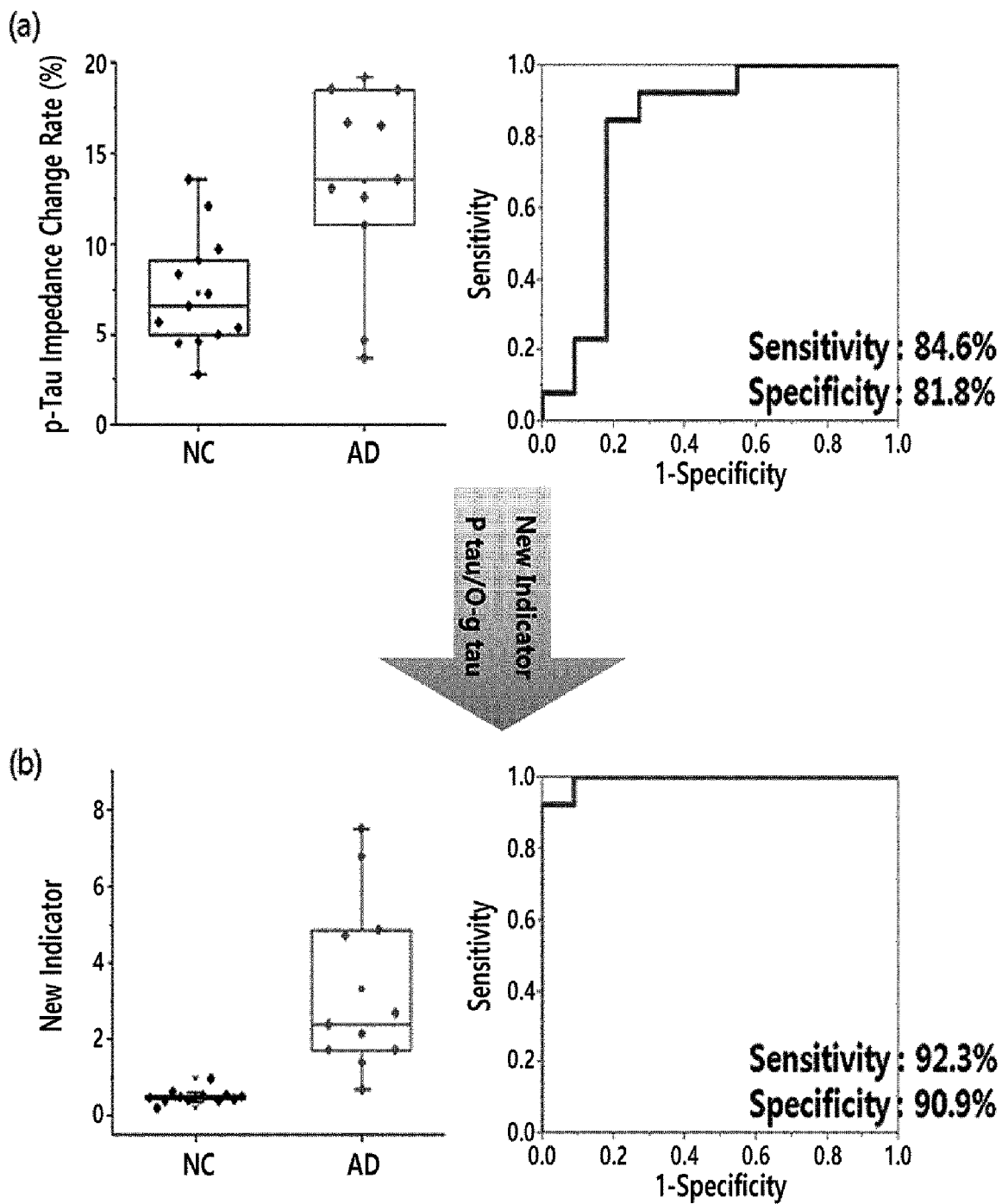
FIG. 20 is a diagram showing the results according to Verification Experiment 10.

The result of the experiment verified that Alzheimer's disease can be diagnosed with higher accuracy by using the change rate of impedance ($Z_1-Z_2/Z_1-Z_3$) of the phosphorylation site of tau protein and the O-glycosylation site of tau protein (sensitivity 92.3%, specificity 90.9%), compared to using the change rate of impedance of the phosphorylation site of tau protein (sensitivity 84.6%, specificity 81.8%) (FIG. 20).

3. Method for Manufacturing Biosensor with Gap

FIGS. 21A to 21G are cross-sectional views illustrating a method for manufacturing the sensor 100 of the system for monitoring post-translational modification of proteins according to one embodiment of the present disclosure.

Figure 21A:
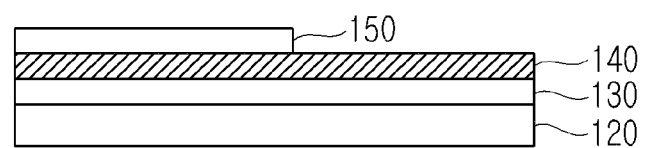
FIGS. 21A to 21G are view provided to explain a method for manufacturing a sensor with a nanogap according to an exemplary embodiment.

Referring to FIG. 21A, the inorganic insulating layer 130 is formed on the substrate 120. The first metal layer 140 is formed on the inorganic insulating layer 130. The first photoresist pattern 150 is formed on the first metal layer 140.

For example, the substrate 120 may include silicon, glass, quartz, polymer, and the like.

For example, the inorganic insulating layer 130 may include an insulating material such as silicon oxide or silicon nitride.

The first metal layer 140 may include gold, silver, platinum, chromium, copper, titanium, alloys thereof, and the like, and may have a single layer or a laminated structure of different metal layers. In one embodiment, the first metal layer 140 may have a two-layer structure of chrome/gold.

The first photoresist pattern 150 partially covers the first metal layer 140, thus partially exposing an upper surface of the first metal layer 140.

Figure 21B:
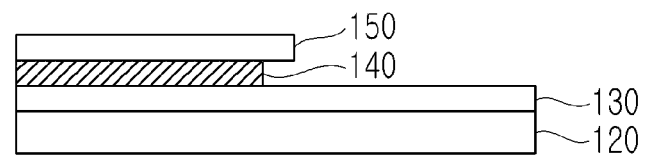

Referring to FIG. 21B, the first metal layer 140 is etched to form the first electrode 140. Etching is isotropic etching by wet etching. Accordingly, the first electrode 140 forms an undercut for the first photoresist pattern 150.

Figure 21C:
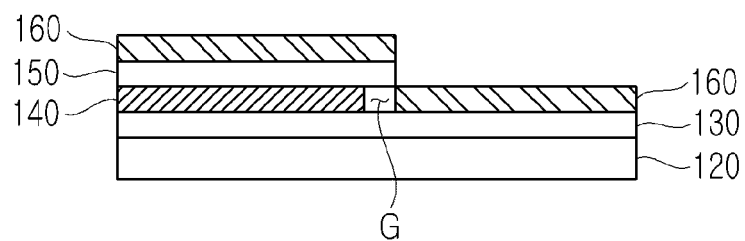

Referring to FIG. 21C, the second metal layer 160 is formed on the first photoresist pattern 150 and the exposed upper surface of the inorganic insulating layer 130. The second metal layer 160 may be formed by deposition such as sputtering, atomic beam evaporation, or the like, and is not formed under the first photoresist pattern 150 on which the undercut is formed.

The second metal layer 160 may include gold, silver, platinum, chromium, copper, titanium, alloys thereof, and the like, and may have a single layer or a laminated structure of different metal layers. In one embodiment, the second metal layer 160 may have a two-layer structure of chrome/gold.

Figure 21D:
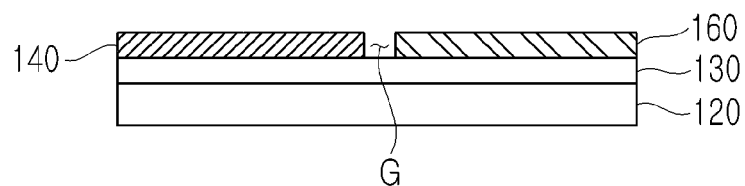

Referring to FIG. 21D, the first photoresist pattern 150 and the second metal layer 160 disposed thereon are removed. Accordingly, a gap G is formed between the first electrode 140 and the remaining second metal layer 160. Since nanogap is not formed by etching using a mask after exposure of photolithography process, but is formed by lift-off after formation of the undercut, the nanogap can be smaller than the critical dimension of the photolithography, and a wafer-level large area processing is possible.

Figure 21E:
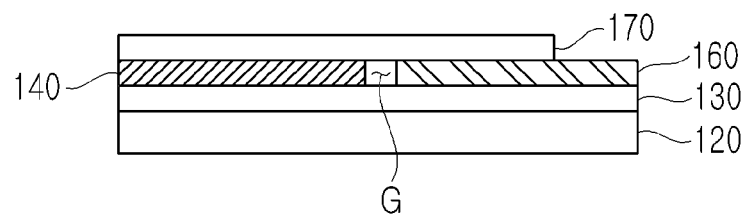

Referring to FIG. 21E, a second photoresist pattern 170 is formed on the first electrode 140 and the remaining second metal layer 160. The second photoresist pattern 170 may cover the gap G and partially expose the second metal layer 160.

Figure 21F:
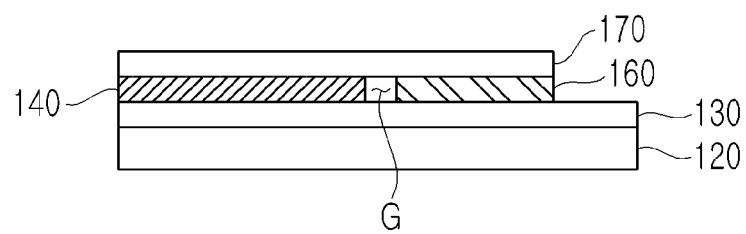

Referring to FIG. 21F, the remaining second metal layer 160 is etched by using the second photoresist pattern 170 as a mask to form the second electrode 160.

Figure 21G:
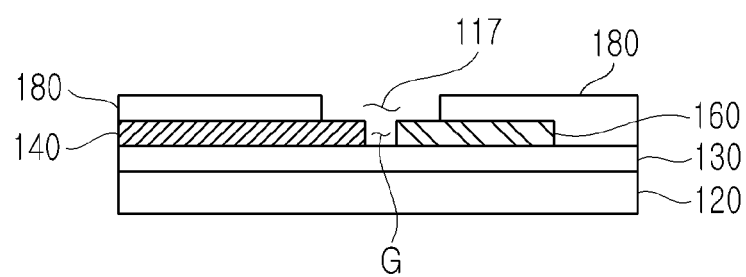

Referring to FIG. 21G, an organic insulating layer 180 is formed on the first electrode 140 and the second electrode 160. The organic insulating layer 180 may form an opening 117 exposing the gap G.

It will be apparent to those skilled in the art that various modifications and variations can be made to the present disclosure without departing from the spirit and scope of the present disclosure as defined by the following claims and their equivalents. Accordingly, the scope of protection of the present disclosure should be determined by the claims.

What is claimed is:

1. A system for monitoring post-translational modification of protein comprising:
   a sensor (100) comprising a plurality of measuring units (110), each including a first electrode (140), a second electrode (160) spaced apart from the first electrode (140) by a predetermined distance to form a gap (G) therebetween, and an organic insulating layer (180) covering a portion of the first electrode (140) and a portion of the second electrode (160) to form an opening (117) communicating with the gap (G); and
   a controller (200) comprising a power supply (220) for applying a predetermined voltage between the first electrode (140) and the second electrode (160) of all of the plurality of measuring units (110), an impedance measuring unit (230) that measures impedance (Z) of an electric circuit in which the power supply (220) and the sensor (100) are electrically connected to each other, and a calculation unit (240) that calculates a change rate of impedance (ΔZ) by a predetermined method based on the impedance (Z) measured by the impedance measuring unit (230),
   wherein the gap (G) between the first electrode (140) and the second electrode (160) is equal to or less than 1 μm,
   wherein each of the measuring units (110) is connected to a first longitudinal main wire (111) and a second longitudinal main wire (114) which are parallel to each other and applied with the predetermined voltage,
   a plurality of first transverse main wires (112) are branched from the first longitudinal main wire (111),
   a plurality of first longitudinal sub wires (113) are branched from each of the first transverse main wires (112),
   the first longitudinal sub wire (113) is electrically connected to the first electrode (140),
   a plurality of second transverse main wires (115) are branched from the second longitudinal main wire (114),
   a plurality of second longitudinal sub wires (116) are branched from each of the second transverse main wires (115), and
   the second longitudinal sub wire (116) is electrically connected to the second electrode (160),
   wherein a target substance placed in the gap (G) comprises:
   a first conjugate (S1) comprising the microbead (b) and a first antibody (10) bound to the microbead (b);

a second conjugate (S2) comprising the microbead (b), the first antibody (10) bound to the microbead (b), and a target protein (20) bound to the first antibody (10);

a third conjugate (S3) comprising the microbead (b), the first antibody (10) bound to the microbead (b), the target protein (20) bound to the first antibody (10), and a second antibody (30) bound to a first modified part of the target protein (20); and a fourth conjugate (S4) comprising the microbead (b), the first antibody (10) bound to the microbead (b), the target protein (20) bound to the first antibody (10), and a third antibody (40) bound to a second modified part of the target protein (20), and a diameter of the opening (117) is twice the diameter of the microbead (b), and wherein, when Z1 is an impedance measured when a first sample including the second conjugate (S2) is introduced into the sensor (100), Z2 is an impedance measured when a second sample including the third conjugate (S3) is introduced into the sensor (100), and Z3 is an impedance measured when a third sample including the fourth conjugate (S4) is introduced into the sensor (100), the change rate of impedance ($\Delta Z$) calculated by the calculation unit (240) is calculated as (Z1−Z2)/(Z1−Z3), wherein the microbead (b) is a magnetic bead, and an amount of the first modified part of the target protein (20) and an amount of the second modified part of the target protein are inversely proportional to each other.

2. The system for monitoring post-translational modification of protein according to claim 1, wherein the impedance (Z) of the sample placed in the gap (G) decreases as an amount and type of the sample bound to the microbead (b) increases.

3. The system for monitoring post-translational modification of protein according to claim 1, wherein the controller (200) further comprises a database (250) for storing the change rate of impedance ($\Delta Z$) calculated by the calculation unit (240), and the calculation unit (240) further calculates comparison result data by comparing a change rate of impedance ($\Delta Z_1$) calculated at a first time point and a change rate of impedance ($\Delta Z_2$) calculated at a second time point after the first time point.

4. The system for monitoring post-translational modification of protein according to claim 1, the system further comprises a magnetic body (300) for guiding the magnetic bead through the opening (117) so that the magnetic bead is placed in the gap (G).

5. The system for monitoring post-translational modification of protein according to claim 1, wherein the target protein (20) is a tau protein.

6. The system for monitoring post-translational modification of protein according to claim 5, wherein the first modified part of the target protein (20) includes a phosphorylation site and the second modified part of the target protein (20) includes an O-glycosylation site.

7. The system for monitoring post-translational modification of protein according to claim 6, wherein the second antibody (30) is an antibody which binds to the phosphorylation site of the target protein (20), and the third antibody (40) is an antibody which binds to the O-glycosylation site of the target protein (20).

* * * * *